United States Patent [19]
Hashiguchi

[11] Patent Number: 6,063,103
[45] Date of Patent: May 16, 2000

[54] ENDOSCOPE FORCEPS

[75] Inventor: Toshihiko Hashiguchi, Sagamihara, Japan

[73] Assignee: Olympus Optical Co., Ltd., Tokyo, Japan

[21] Appl. No.: 09/123,872

[22] Filed: Jul. 28, 1998

[30] Foreign Application Priority Data

Jul. 24, 1998 [JP] Japan ................... 10-209386

[51] Int. Cl.[7] ................................. A61B 17/28
[52] U.S. Cl. ............................................ 606/205
[58] Field of Search .................... 606/205, 206, 606/207, 208

[56] References Cited

U.S. PATENT DOCUMENTS

| 2,113,246 | 4/1938 | Wappler .................... 606/205 |
| 5,906,630 | 5/1999 | Anderhub et al. ............ 606/205 |

FOREIGN PATENT DOCUMENTS

| 0484671 B1 | 5/1992 | European Pat. Off. . |
| 4-246344 | 9/1992 | Japan . |
| 6-285078 | 10/1994 | Japan . |

*Primary Examiner*—Michael Buiz
*Assistant Examiner*—Vy Q. Bui
*Attorney, Agent, or Firm*—Frishauf, Holtz, Goodman, Langer & Chick, P.C.

[57] ABSTRACT

An endoscope forceps of the present invention comprises an operating section for inputting an operating force, an insertion section, which is fixedly connected to the operating section, and which can be inserted into a channel of an endoscope, an operating rod, which is inserted in the insertion section so as to be movable forward or backward, one end of which is connected to the operating section, and which is moved forward or backward by the operating force input to the operating section, and a forceps section which is disposed at the fore end of the insertion section, wherein the forceps section comprises a first jaw pivotably mounted at the other end of the operating rod with a first pivotal shaft engaging with both, and a second jaw pivotably mounted at the fore end of the inserting section with a second pivotal shaft engaging with both, and the first jaw and the second jaw are pivotably mounted to each other with a third pivotal shaft engaging with both.

12 Claims, 22 Drawing Sheets

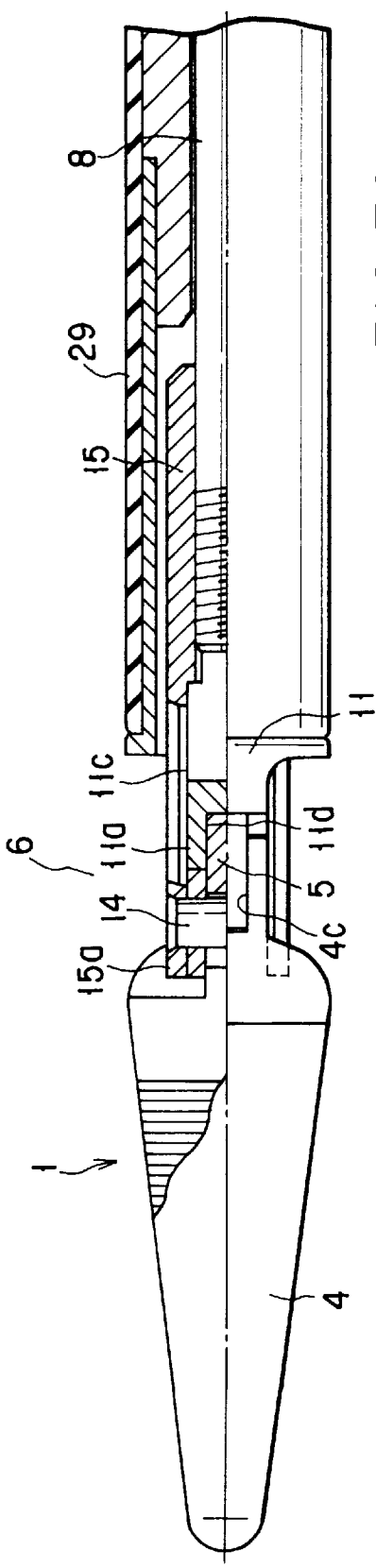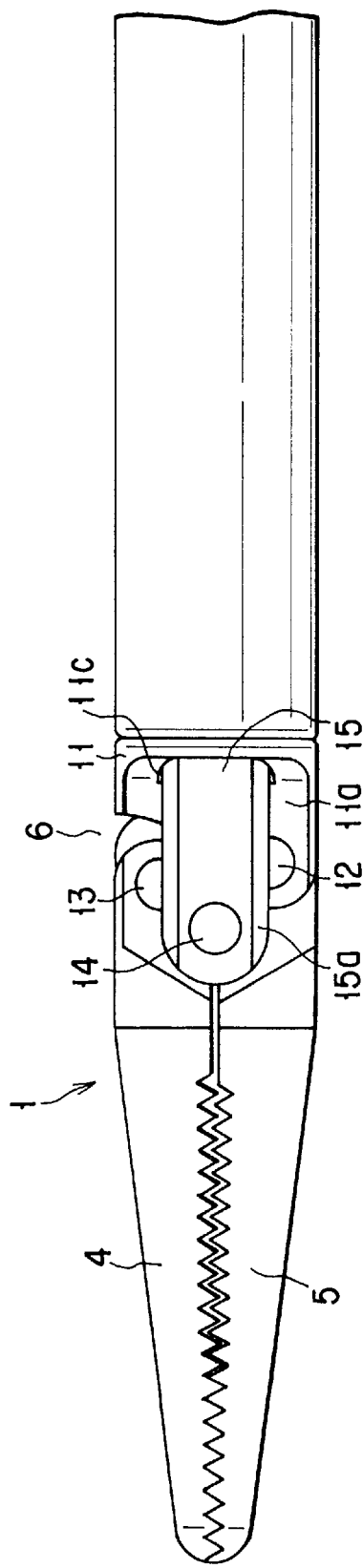

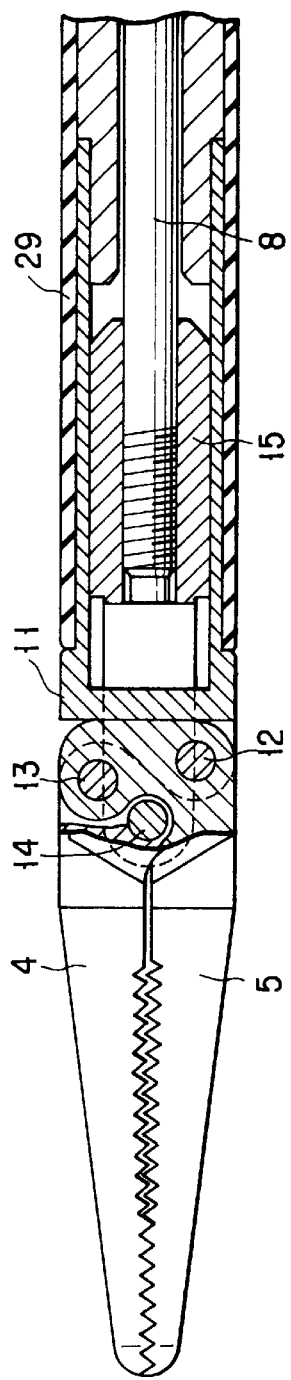
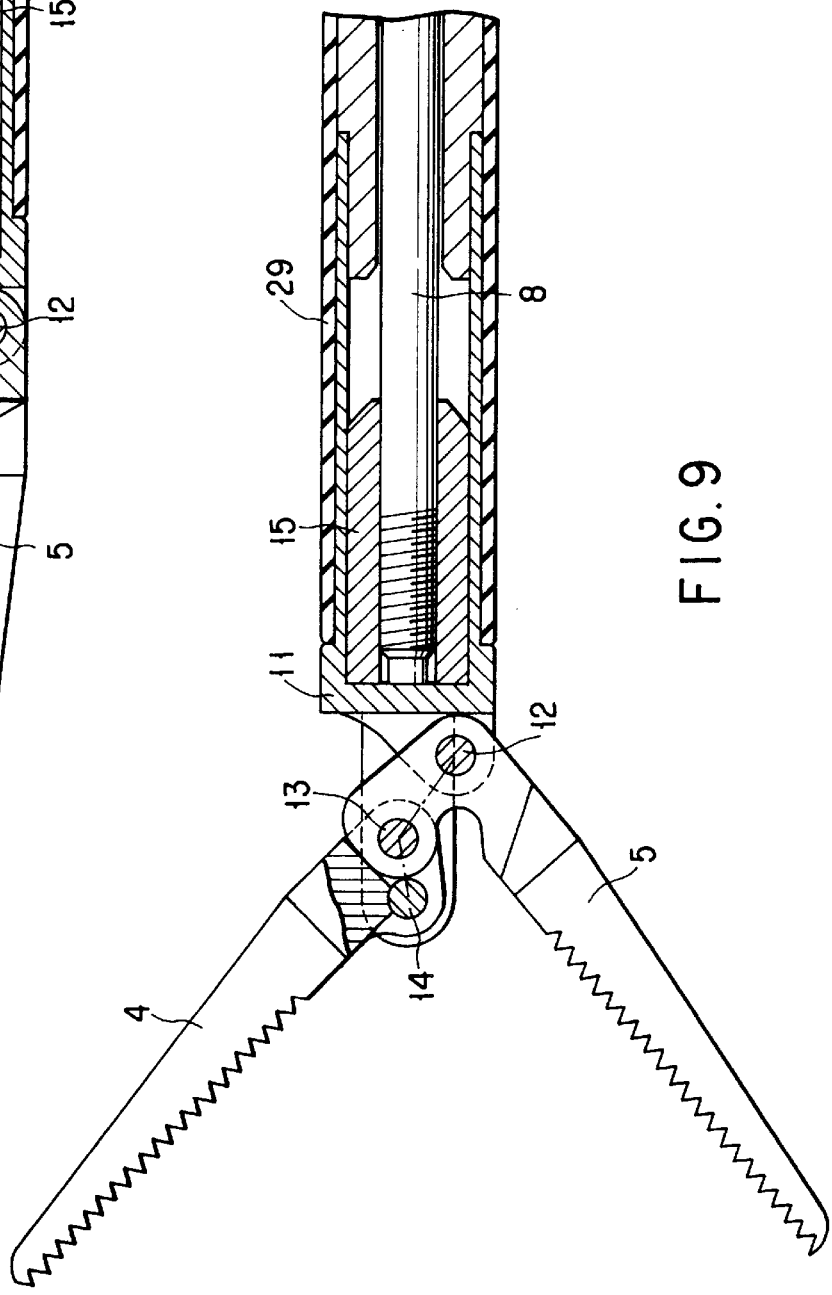
FIG. 8
FIG. 9

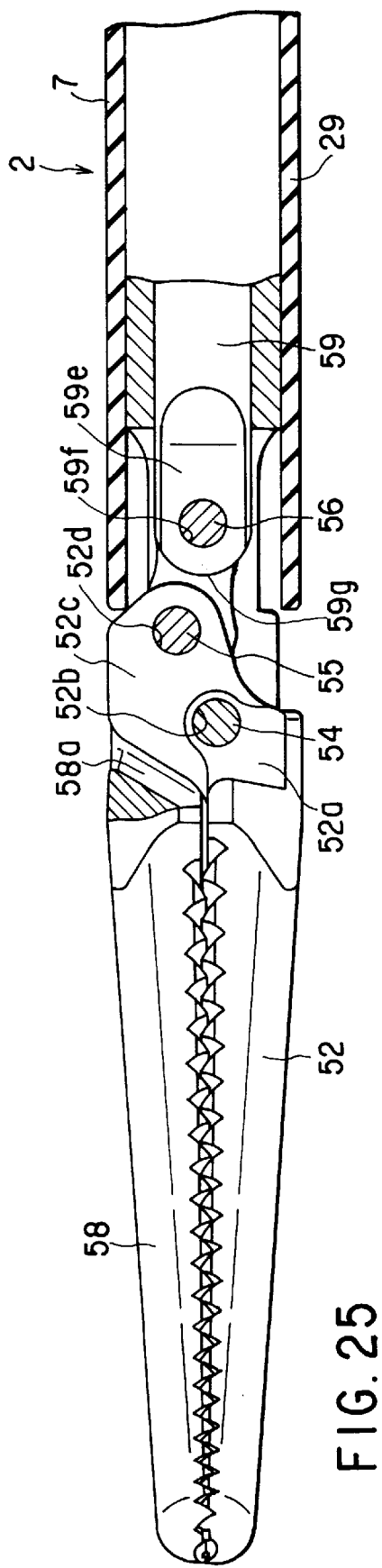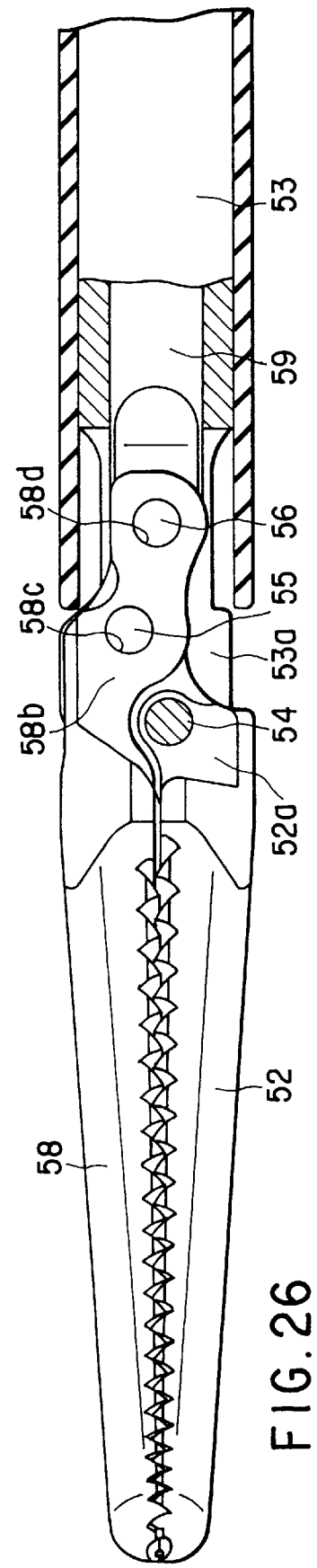
FIG. 25
FIG. 26

ENDOSCOPE FORCEPS

BACKGROUND OF THE INVENTION

The present invention relates to an endoscope forceps used together with an endoscope for grasping or tearing off tissue or the like of an organism.

An endoscope forceps for grasping or tearing off tissue or the like of an organism is disclosed in, for example, EP 0484671B1 (the Jpn. Pat. Appln. KOKAI Publication No. 4-246344), the Jpn. Pat. Appln. SHUTSUGAN Publication No. 5-78253 or the like.

An endoscope forceps disclosed in EP 0484671B1 comprises a handle assembly, a body assembly and a device mechanism. The handle assembly is constructed from a stationary handle and a pivoting handle. The body assembly is constructed from an outer tubular member and an inner rod member, and is fixed to the handle assembly at an end thereof, wherein the inner rod member has a bearing surface and is slidably disposed in the outer tubular member. The inner rod member is adapted for sliding in response to a movement of the pivoting handle in a condition that the body assembly is fixed to the handle assembly. The device mechanism is constructed from one pair of jaws each of which has a cam surface to engage with the bearing surface of the inner rod member in a freely slidable manner and a support member to support the one pair of jaws. In such a structure, when the pivoting handle is moved, the inner rod member is slid relatively to the outer tubular member. Thereby, the bearing surface of the inner rod member and the cam surface of the device mechanism, which engage with each other, relatively slide in a longitudinal direction to make the one pair of jaws pivot (opened or closed).

The endoscope forceps disclosed in EP 0484671B1 has problems as shown below:

(1) the structure is complex, it is hard to attain a desired mechanical strength and its production cost is high;

(2) since many sliding parts are included and in addition, sliding lengths are large, abrasion cannot be avoided, and especially in autoclave sterilization, since lubrication by fat and oil cannot be expected, movements are not smooth and thereby abrasion is accelerated;

(3) when the jaws get opened, the base end sections of the jaws where cam grooves are formed protrude out beyond the outer diameter of the support member, therefore, the base ends of the jaws cannot be covered with an electrically insulating member, which causes a metal portion widely exposed at the fore end of the forceps, and furthermore which produces a fear of burning of an unintended portion in cauterization by means of high frequency heating; and (4) an opening/closing drive mechanism for the forceps is disposed inside the support member which is located closer to the base end of forceps than a pivoting axis thereof and therefore, the opening/closing drive mechanism is hard to be cleaned.

An endoscope forceps disclosed in the Jpn. Pat. Appln. SHUTSUGAN Publication No. 5-78253, on the other hand, are provided with a forceps opening/closing drive mechanism in the form of a quadric crank chain as shown in FIGS. 34 and 35. FIG. 34 shows a relation between an operating force F and a grasping force f in a condition where one pair of jaws c, c is perfectly closed. Since an angle of inclination of a link a is small, as shown in the figure, a component F' of a force F pulling an operating shaft b is small. Consequently, a component F'' of the component F' in a rotational direction of a jaw c is also small and a moment M which rotates the jaw c is very small. As a result, the grasping force f at the fore end of the jaws c, c is very small.

FIG. 35 shows a relation between an operating force F and a grasping force f in a condition where one pair of jaws are perfectly opened. Since an angle of inclination of a link a is large, as shown in the figure, a component F' of a force F pulling an operating shaft b is larger than F. As a result, a component F'' of the component F' in a rotational direction of a jaw c is also as large as the component F' since the component F'' is oriented in nearly the same direction as the component F'.

Therefore, the endoscope forceps disclosed in the Jpn. Pat. Appln. SHUTSUGAN Publication No. 5-78253 has problems as shown below:

(1) when the jaws c, c are perfectly opened, a link a protrudes out beyond an outer diameter of a sheath in which the operating shaft b is inserted, an insulating cover which covers the outer surface of the sheath cannot accordingly be extended up to the fore end of the forceps, for that reason a metal is exposed at the fore end of the forceps and there arises a fear to burn an unintended portion in cauterization by means of high frequency heating and a suture thread, besides, has a chance to catch the link a in a suture operation in which the suture thread is grasped by the jaws if the link a protrudes out beyond the outer diameter of the sheath;

(2) the forceps opening/closing drive mechanism is disposed inside a support member located at a position closer to a base end than pivoting shafts of the jaws c, c, which makes it hard to clean the forceps opening/closing drive mechanism.

BRIEF SUMMARY OF THE INVENTION

An object of the present invention is to provide an endoscope forceps having a simple structure, which is easy to be cleaned, and in which a link mechanism for opening/closing jaws does not protrude out beyond the outer diameter of a support member (or a sheath) to support the jaws, and in which a drive mechanism is less abraded.

The object of the present invention is achieved by the following endoscope forceps, which comprise: an operating section for inputting an operating force; an insertion section, which is fixedly connected to the operating section, and which can be inserted into a channel of an endoscope; an operating rod, which is inserted in the insertion section so as to be movable forward or backward, one end of which is connected to the operating section, and which is moved forward or backward by the operating force input to the operating section; and a forceps section which is disposed at the fore end of the insertion section, wherein the forceps section comprises: a first jaw pivotably mounted at the other end of the operating rod with a first pivotal shaft engaging with both; and a second jaw pivotably mounted at the fore end of the inserting section with a second pivotal shaft engaging with both, and the first jaw and the second jaw are pivotably mounted to each other with a third pivotal shaft engaging with both.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments give below, serve to explain the principles of the invention.

FIG. 7A is a partially sectional top view of a forceps section of an endoscope forceps pertaining to a second embodiment of the present invention;

FIG. 7B is a side view of the forceps section of FIG. 7A;

FIG. 8 is a sectional side view of the forceps section of FIG. 7A in a condition of closed jaws;

FIG. 9 is a sectional side view of the forceps section of FIG. 7A in a condition of opened jaws;

FIG. 25 is a view in a section including a central line of a forceps section of an endoscope forceps pertaining to a seventh embodiment of the present invention;

FIG. 26 is a view in a section including a parallel line offset from the central line of a forceps section of FIG. 25;

DETAILED DESCRIPTION OF THE INVENTION

Embodiments of the present invention will below be described in reference to the accompanying drawing.

Figure 1:
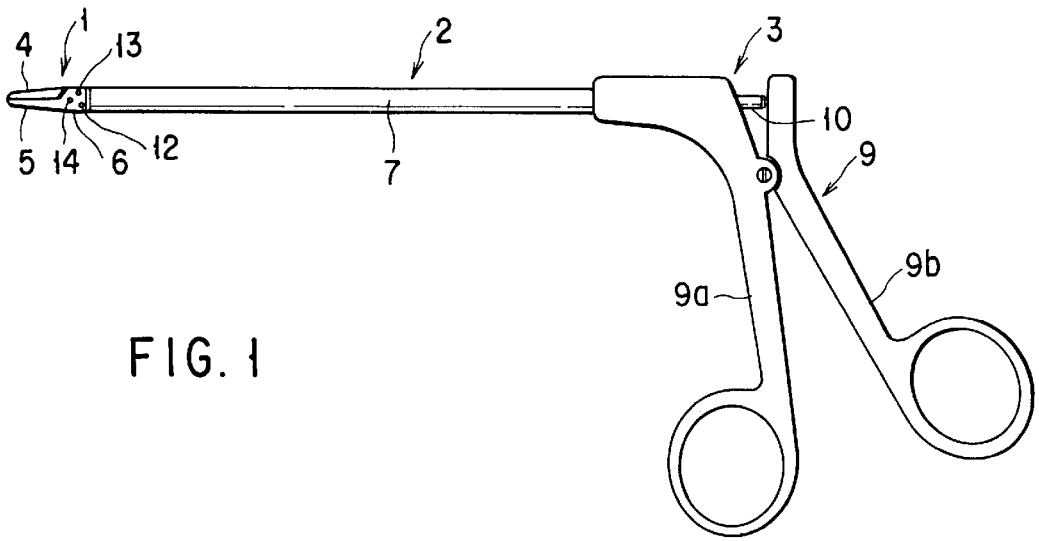
FIG. 1 is a side view of an endoscope forceps pertaining to a first embodiment of the present invention.

FIGS. 1 through 6 show the first embodiment of the present invention. As shown in FIG. 1, an endoscope forceps pertaining to the present embodiment comprises: a forceps section 1; an insertion section 2 which can be inserted into a channel of an endoscope, not shown; and an operating section 3. The forceps section 1 comprises first and second jaws 4, 5 and an opening/closing mechanism 6 to open/close the jaws 4, 5. The insertion section 2, as shown in FIG. 2A, comprises a tubular sheath 7 covered with an insulating tube 29 (see FIG. 4A) and an operating rod 8, which is disposed inside the sheath 7, and which is connected to the opening/closing mechanism 6. The operating section 3, as shown in FIG. 1, comprises handles 9. The handles 9 comprise a stationary handle and a pivoting handle 9b. The operating section 3 comprises a connecting member 10 as an operating force transmitting member which connects the operating rod 8 and the pivoting handle 9b.

Figure 2A:
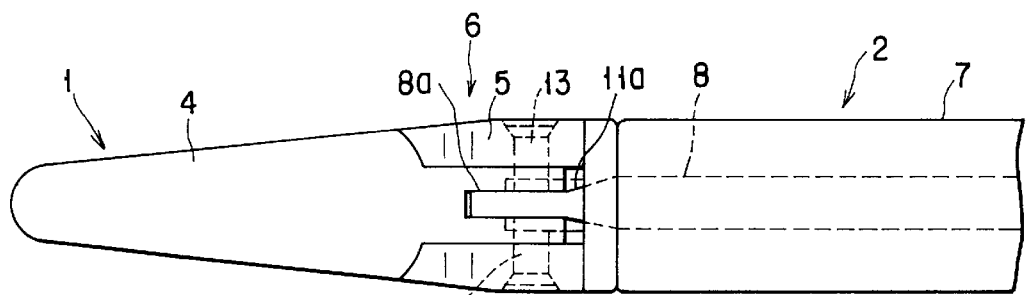
FIG. 2A is a top view of a forceps section of the endoscope forceps of FIG. 1.
Figure 2B:
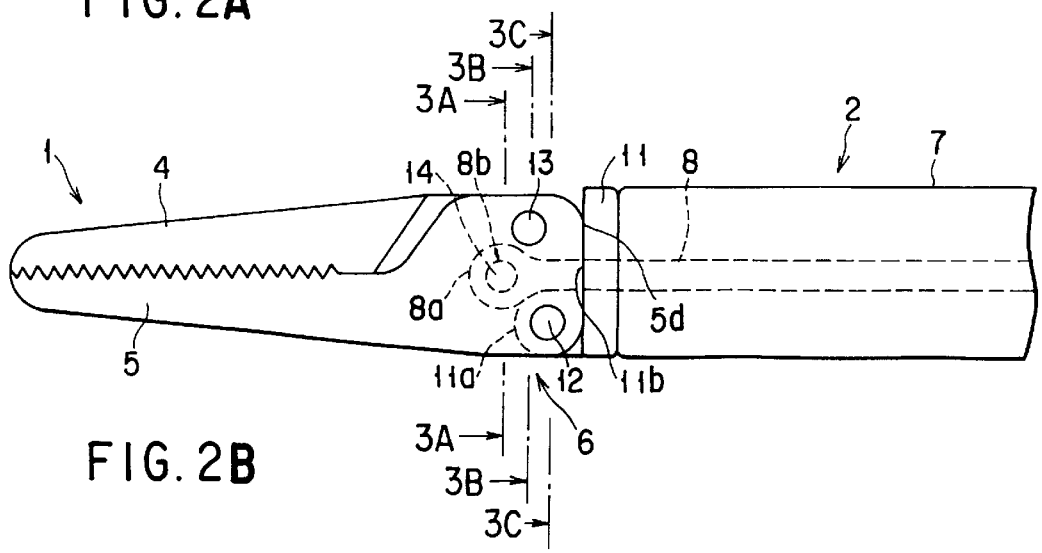
FIG. 2B is a side view of a forceps section of the endoscope forceps of FIG. 1.
Figure 3A:
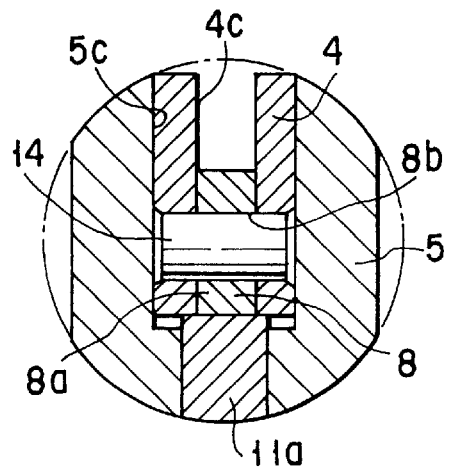
FIG. 3A is a sectional view taken along line 3A—3A of FIG. 2B.
Figure 3B:
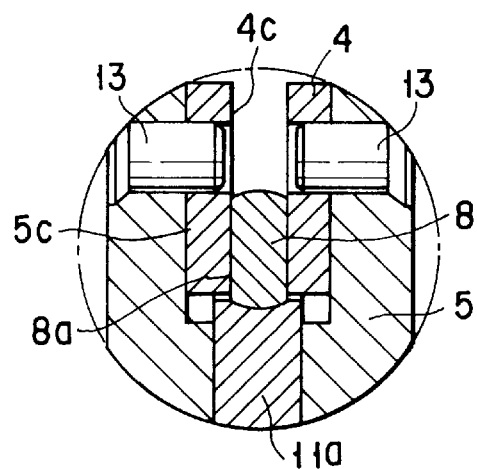
FIG. 3B is a sectional view taken along line 3B—3B of FIG. 2B.
Figure 3C:
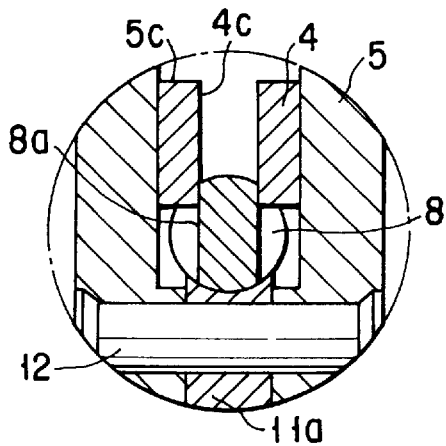
FIG. 3C is a sectional view taken along line 3C—3C of FIG. 2B.

As shown in FIGS. 2A, 2B and 3C, the second jaw 5 is divided into two parts at its base end, a first support section 11a of a support member 11 which is fittingly inserted in the fore end section of the insertion section is held by the two parts in a sandwiching manner and besides, the second jaw 5 is in a freely pivotable manner mounted to the first support section 11a with a second pivotal pin 12 fixed to the second jaw 5 as a second pivotal shaft engaging with the first support member 11a (see FIG. 3C). As shown in a detailed manner in FIG. 3B, a first jaw 4 is fittingly inserted in a slot 5c formed in the base end section of the second jaw 5. Pivotal pins 13 as a third pivotal shaft are respectively mounted to the two parts at the base end of the second jaw 5 which are on both sides of the slot 5c while engaging with the first jaw 4 so that the first jaw 4 can freely pivoted thereabout. In other words, the first jaw 4 is in a freely pivotable manner mounted to the second jaw 5 with the pivotal pin 13 engaging with both. At this point, inner ends of the two pivotal pins 13, 13 do not protrude into a slot 4c formed in the base end section of the first jaw 4 so that movements, forward and backward, of the operating rod 8 may not be prevented by the pivoting movement of the first jaw 4.

Figure 4A:
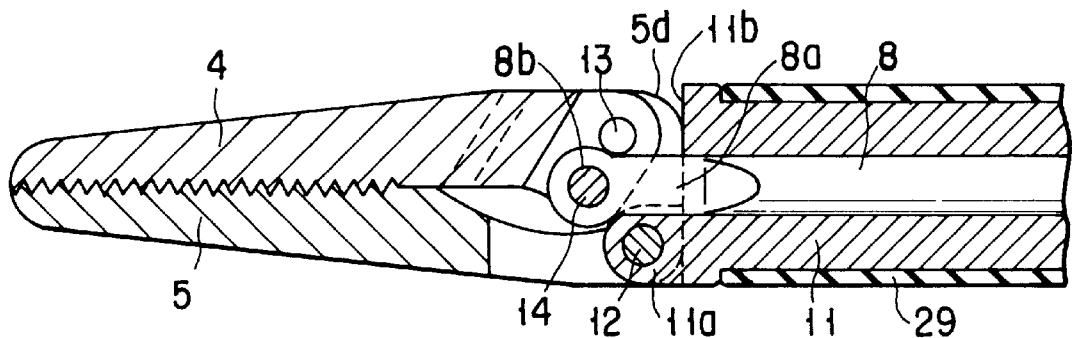
FIG. 4A is a sectional side view of the forceps section of FIG. 2A in a condition of closed jaws.

As shown in FIG. 4A, the operating rod 8, is inserted in an inner hole of the supporting member 11 so that the operating rod 8 may move only along the axial direction, forward or backward. As shown in FIGS. 2A, 2B, 3A and 3B, a fore end section 8a of the operating rod 8 has a flat shape and inserted in the slot 4c of the first jaw 4. The fore end section 8a has a pin inserting hole 8b and a pivotal pin 14 as a first pivotal shaft is inserted in the pin inserting hole 8b. The pivotal pin 14 connects the fore end section 8a of the operating rod 8 and the first jaw 4 in a pivotable manner relatively to each other.

As shown in FIG. 2B, the base end of the second jaw 5, is finished with a flat end surface 5d and a small gap is kept between the flat end surface 5d and the fore end surface 11b of the support member 11. The top surface of the support section 11a assumes a concave surface in conformity with an outer profile of the operating rod 8 in order to prevent deformation of the operating rod 8 as a guide for the operating rod 8 in movement, forward or backward (see FIG. 3B).

Functional movements of the endoscope forceps of the above mentioned structure will be described.

The endoscope forceps are inserted into an abdominal cavity of a patient, for example, through a trocar. Thereafter an operator moves the handles 9 to open or close, thereby the first and second jaws 4, 5 of a forceps section 1 are opened/closed and grasping and tearing off of a target tissue such as organs, a blood vessel, a peritoneum or the like can thus be performed. If the forceps section 1 is formed in the shape of scissors, the target tissue can be cut or torn off by opening/closing the forceps section 1.

Figure 4B:
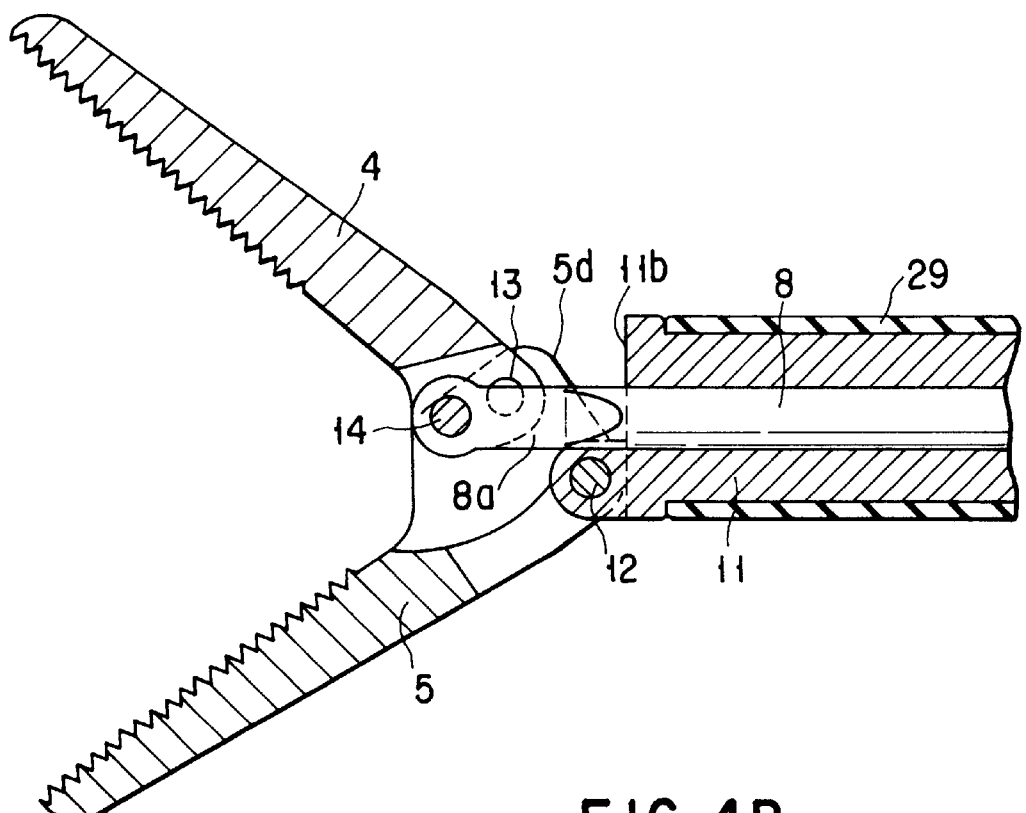
FIG. 4B is a sectional side view of the forceps section of FIG. 2A in a condition of opened jaws.

FIG. 4A shows a condition that the jaws 4, 5 are perfectly closed and FIG. 4B shows a condition that the jaws 4, 5 are perfectly opened. When the operating rod 8 is pushed out along a leftward direction in the figure, the pivotal pin 14 located at the base end section of the first jaw 4 moves along the leftward direction and a leftward force is transmitted to the second jaw 5 with the help of the pivotal pin 13. Thereby, the second jaw 5 is adapted to be turned counterclockwise about the pivotal pin 13 as a center which is a connection section with the support section 11a. At this point, the first jaw 4 receives a leftward force by the operating rod 8 and a rightward force by a reaction from the jaw 5. The leftward and rightward forces are integrated to be a couple of forces to act on the first jaw 4 to turn clockwise. As a result, the first and second jaws 4, 5 are respectively turned in opposed directions so that both move away form each other. That is, the jaws 4, 5 are opened. Only if a reverse operation is conducted, that is, only if the operating rod 8 is pulled along the rightward direction, the jaws 4, 5 are closed.

When the jaws 4, 5 are perfectly closed as shown in FIG. 4A, in other words when the fore ends of the first and second jaws 4, 5 are in contact with each other, the flat end surface 5b of the base end of the second jaw 5 is kept slightly spaced apart from the fore end surface 11d of the support member 11. If a pulling force acting on the operating rod 8 in the rightward direction is further increased in this condition, the jaws 4, 5 receive elastic deformation and thereby the end surfaces 5d, 11d comes to be in contact with each other. At this point, the pulling force to act on the operating rod 8 in the rightward direction is fully stopped by the supporting member 11 and thereby the jaws 4, 5 are not affected by the pulling force in the rightward any longer. In other words, not only is breakage of the jaws 4, 5 prevented from occurring but the jaws 4, 5 are positioned so as to assume a perfectly closed condition that the jaws 4, 5 are aligned straight toward the fore end side.

When the jaws 4, 5 are perfectly opened as shown in FIG. 4B, and bending forces are simultaneously imposed on the jaws 4, 5 upwardly or downwardly, the fore end of the operating rod 8 receives a force F1 which acts thereon so as to be moved upwardly or downwardly. In the embodiment, since the operating rod 8 is fittingly inserted inside of the support member 11 without any play, the operating rod 8 has a chance to be bend by the force F1. For this reason, in the embodiment, the operating rod is reinforced with a sufficient strength and therefore the operating rod 8 is designed not to be bent by the force F1. That is, the first and second jaws 4, 5 are designed not to be displaced upwardly or downwardly with ease.

In the embodiment, the three pivotal pins 12, 13, 14 are disposed assuming the positional relations as shown in FIGS. 1 through 4B and thereby the first and second jaws 4, 5 are almost equally opened/closed with respective movements upward and downward or vice versa. However, if the shape of a triangle formed by connecting the three pivotal pins 12, 13, 14 with straight lines is changed, it is possible that the first and second jaws 4, 5 can be opened/closed in an unequal manner. In other words, a behavior of opening/ closing of the jaws can arbitrarily changed according to a purpose and, for example, there can be possible double-opening forceps whose jaws are both opened or single-opening forceps only one of whose jaws is opened and thereby forceps can be adapted in a various ways of application.

There is no specific limitation to structures of parts and configuration thereof in the first and second jaws 4, 5 which are determined in terms of positions in reference to the operating rod 8 and the supporting member 11 in the embodiment. If the structures and configuration are properly changed, a moving direction of the operating rod 8 in company with an opening/closing operation can be reversed.

Figure 5:
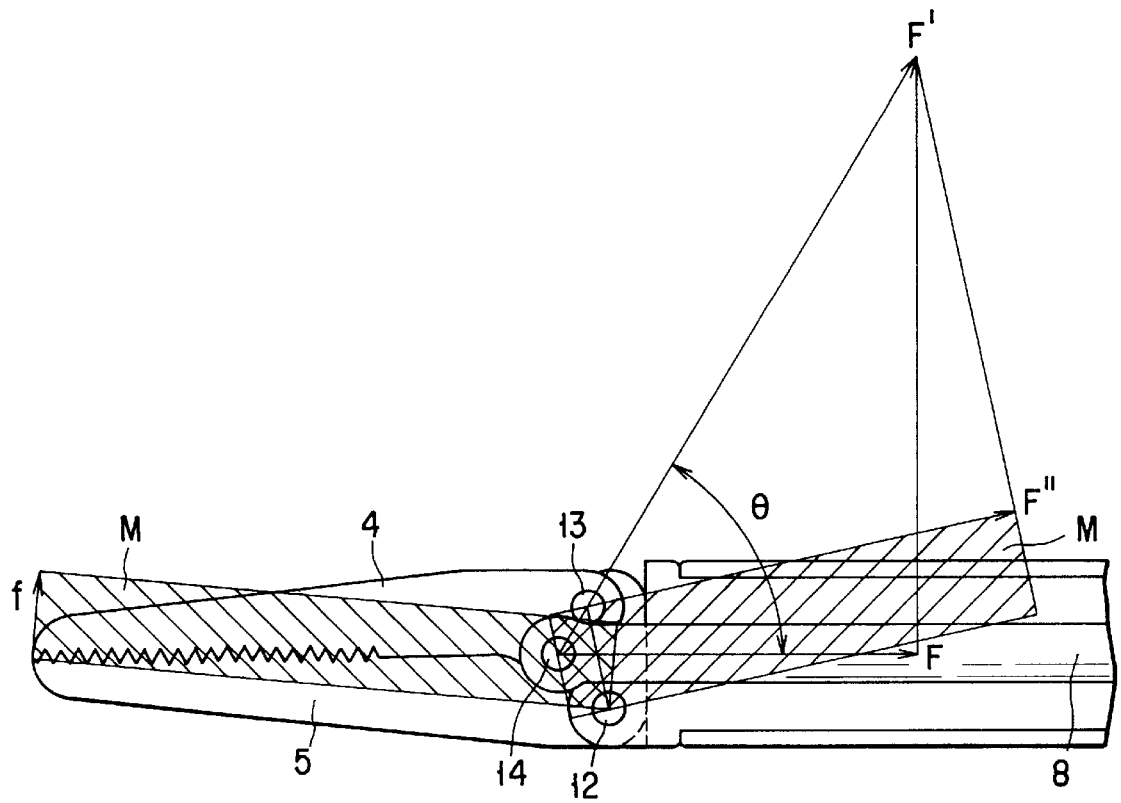
FIG. 5 is a diagram of a dynamic analysis showing a relation between an operating force F and a grasping force f in a condition of perfectly closed jaws in the forceps section of FIG. 2A.
Figure 6:
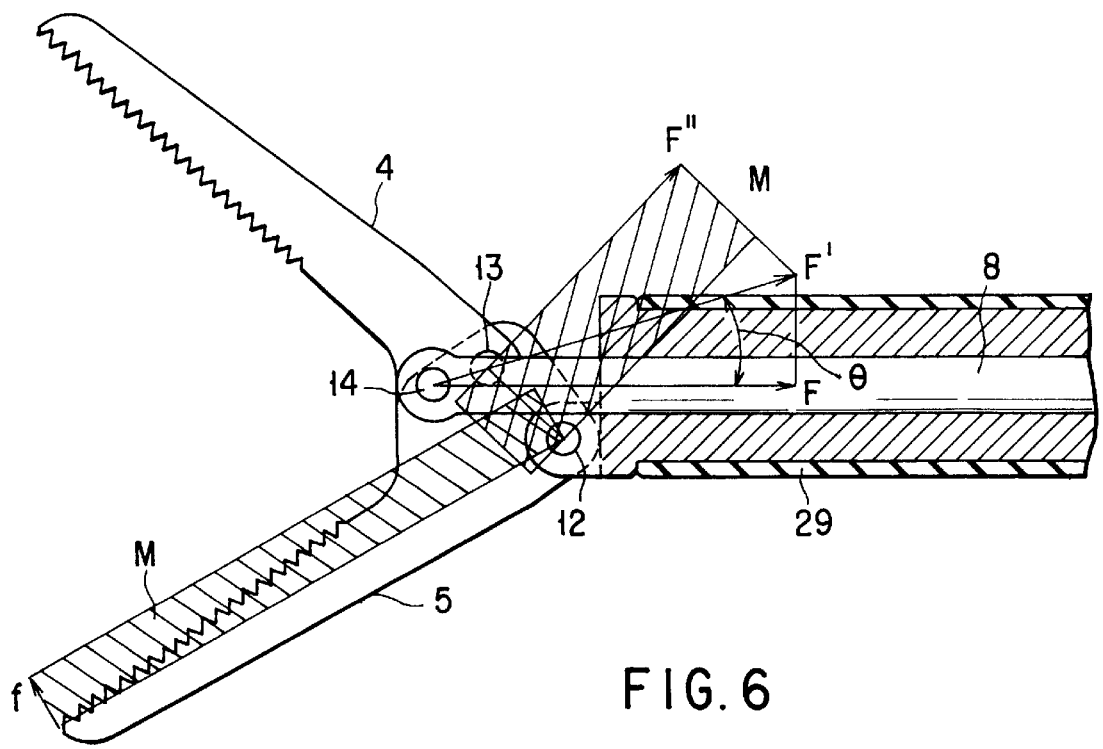
FIG. 6 is a diagram of a dynamic analysis showing a relation between an operating force F and a grasping force f in a condition of perfectly opened jaws in the forceps section of FIG. 2A.
Figure 10:
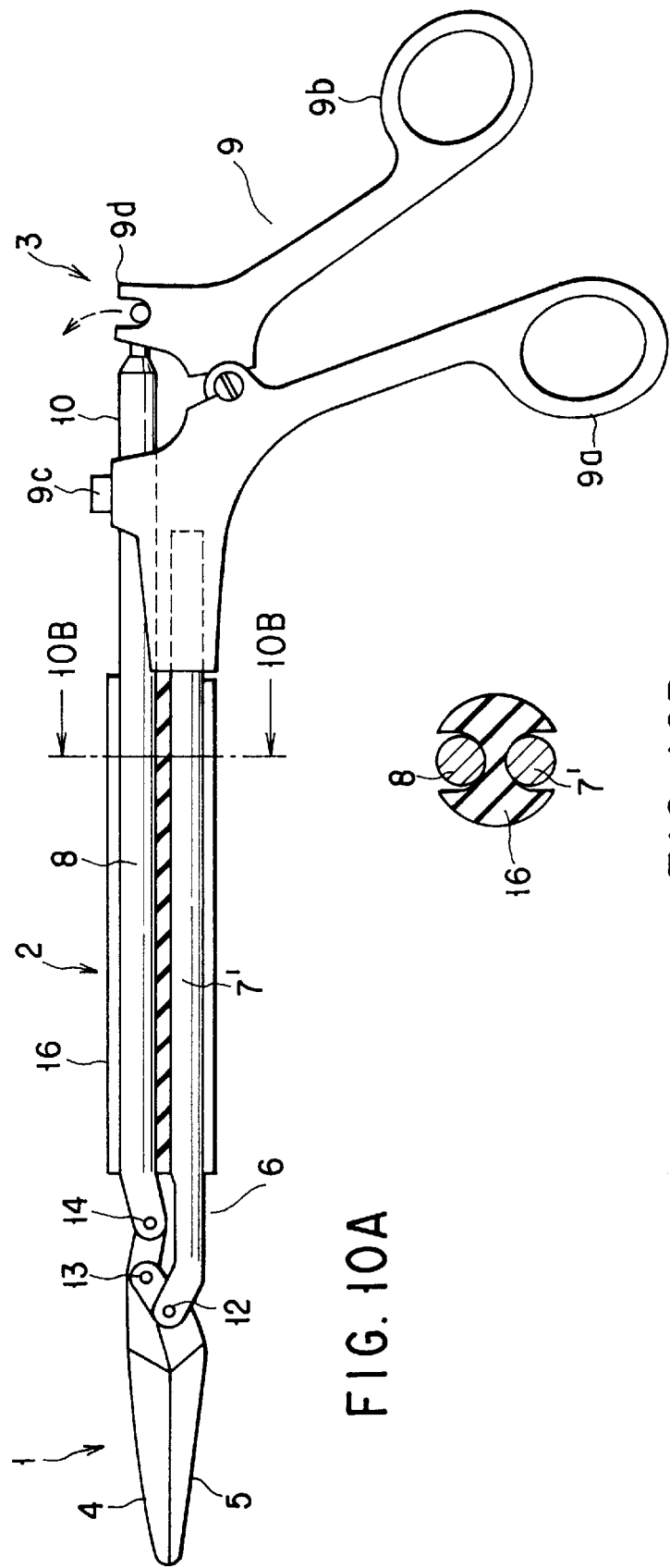
FIG. 10A is a side view of a pair of endoscope forceps pertaining to a third embodiment of the present invention.
FIG. 10B is a sectional view taken along line 10B—10B of FIG. 10A.

The opening/closing movements of the first and second jaws 4, 5 will be analyzed from the view point of dynamics, which goes in the following way. FIG. 5 shows a condition that the jaws 4, 5 are perfectly closed and FIG. 6 shows a condition that the jaws 4, 5 are perfectly opened. The force F1 acting on the operating rod 8 in the rightward direction, as shown in FIG. 5, is transmitted to the second jaw 5 through the first jaw 4. A force F is decomposed into a component force F' in a direction of a line connecting the pivotal pin 13 and the pivotal pin 14 and a component force directing right downwardly. Since the right downward component force is offset with a reaction force acting on the operating rod 8 right upwardly from the support member 11, it is not shown in the figure. Since an angle θ formed between a direction of a line connecting the pivotal pins 13, 14 and the axial direction (a direction of the force F) of the operating rod 8 is large, a component force F' is larger than a force F. The larger the angle θ is, the larger the component force F' is, and since the component force F' approaches infinity, which is not practical, if the angle assumes 90°. A moment M which turns the second jaw 5 is a product of a component F'' of the component force F' multiplied by a distance between the pivotal pins 13, 12. Therefore, a grasping force f at the fore end of the second jaw 5 is a quotient of the moment M divided by the distance between the fore end of the second jaw 5 and the pivotal pin 12.

Figure 34:
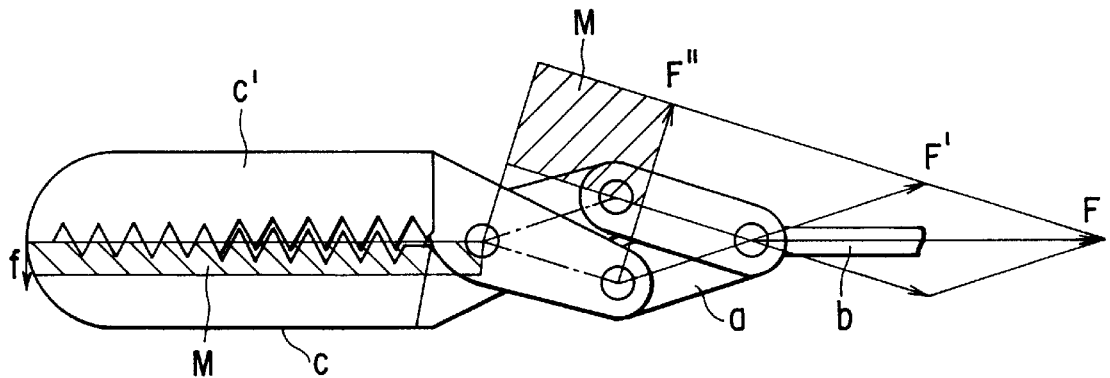
FIG. 34 is a side view of conventional endoscope forceps.
Figure 35:
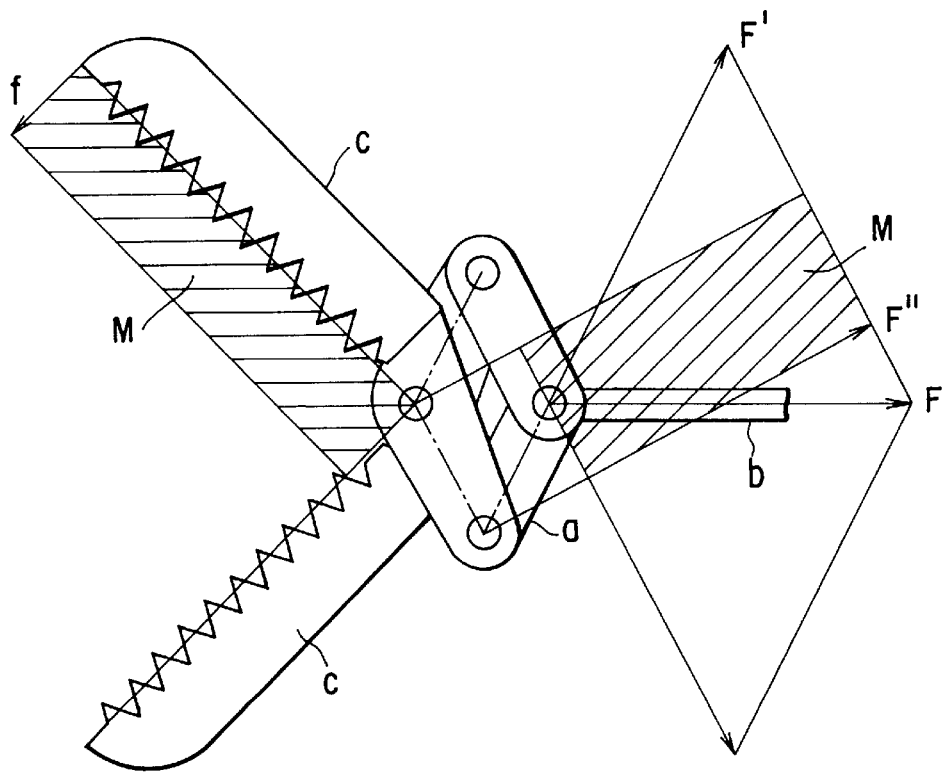
FIG. 35 is a side view of the forceps section of FIG. 34 in a condition of opened jaws.

A conventional technique shown in FIG. 34 and the embodiment shown in FIG. 5 is compared when an operating force F is the same and as a result, in the conventional technique, though the technique is advantageous in production of a force at the fore end because of a short jaw c, a grasping force f is, actually, smaller than the embodiment by a great margin. When the jaws 4, 5 are perfectly opened as shown in FIG. 6 in the embodiment, an angle θ is small and therefore, a component force F' is smaller as compared with the case of a condition of perfectly closed jaws of FIG. 5. Therefore, the grasping force f at the fore ends of the jaws 4, 5 are also smaller.

The mechanics of the embodiment will the oretically be studied from the view point of mechanics. There are four links between the first and second jaws 4, 5, the operating rod 8 and the support member 11 and revolute pairs are found between the first and second jaws 4, 5, between the first jaw 4 and the operating rod 8 and between the second jaw 5 and support member 11, and a sliding pair is found between the operating rod 8 and the support member 11.

The following effects can be obtained, as mentioned above, according to the endoscope forceps of the embodiment:

(1) since the forceps of the embodiment can open/close the jaws 4, 5 without use of intermediate links which only works to transmit forces as in the case of the quadric crank chain shown in FIG. 34, a structure is simple, excellent in strength and reliability and low in cost;

(2) since an opening/closing mechanism for opening/closing the jaws 4, 5 is not disposed at a position closer to the basic end than the pivotal shaft 12 disposed between the jaws 5 and the supporting member 11, in other words, since the opening/closing mechanism is disposed between the jaws 4, 5 and the mechanism is widely exposed when the jaws 4, 5 are opened, cleaning is easy; and (3) since structural elements of the forceps section 1 do not protrude out beyond the outer diameter of the insertion section 2 by opening/closing operations for opening/closing the jaws 4, 5, there is no fear to burn other portions than an target organ in cauterization by means of high frequency heating and simultaneously there is no chance where a suture thread catches a structural element of the forceps 1 when a suture operation is conducted while the suture thread is grasped by the jaws (,which makes ligation in a body cavity easy).

FIGS. 7A through 9 shows the second embodiment of the present invention. The same structural parts as those in the first embodiment are indicated by the same marks in the embodiment and description is omitted thereon.

FIGS. 7A and 7B are show the forceps section 1 of an endoscope forceps pertaining to the embodiment. In the endoscope forceps of the embodiment, as shown in the figure, a force from an operating rode 8 is not transmitted to first and second jaws 4, 5 in the vicinity of the axial line as in the first embodiment, but the force from the operating rod 8 is transmitted to the jaws 4, 5 at an outer position from the axial line. In a concrete manner, a support member 11a is disposed in the center of a support section 11, a fore end section 15a consisting of two parts of a connecting member 15 extends toward the fore end from slits 11c formed on the both sides of a support member 11a. The connecting member 15 is connected to an operating rod 8. A slot 11d is formed in the support section 11a. The base end section of the second jaw 5 is fittingly inserted in the slot 11d and pivotably mounted to the support section 11a with a pivotal pin 12 engaging with both.

The second jaw 5 is fittingly inserted in a slot 4c formed at the based end side of the first jaw 4 and connected with the first jaw 4 with a pivotal pin 13 engaging with both. In this case, the pivotal pin 13 is a single pin which is not divided into two parts, which is different from the case of the first embodiment (where two-piece pins are used.) The first jaw 4 and the connecting member 15 is pivotably connected with a pivotal pin 14 engaging with both.

Opening/closing operations of the first and second jaw 4, 5 are basically similar to those in the first embodiment. However, an operating force of the operating rode 8 is transmitted to the jaw 4 by way of the connection member 15 at an outer position from the axial line (see FIGS. 8 and 9).

Therefore, the following effects can be obtained according to the pair of endoscope forceps of the present invention:

(1) since the operating rod 8 does not penetrate on the central axis of the jaws 4, 5, there is less limitation to sizes and locations of the pivotal pins 12, 13, 14 and it is possible to increase the sizes and strength thereof; and (2) since there is no necessity for the operating rod 8 to penetrate through between divided pivotal pins 13 as in the first embodiment, fabrication is easy and high precision can be attained with ease.

FIGS. 10A through 12 show the third embodiment of the present invention. The same structural parts as those in the first embodiment are indicated by the same marks in the embodiment and description is omitted thereon.

In the endoscope forceps of the embodiment, as shown in FIG. 10A, a insertion section 2 is constructed from a rod-like stationary rod 7' different from a tubular sheath 7 as in the first embodiment. An operating rod 8 is disposed in parallel to the stationary rod 7'. Sectional shapes of the operating rod 8 and the stationary rod 7' are not limited to a circle as shown in FIG. 10B, but, for example, a semicircle, a rectangle, an ellipse, or the like may be used instead.

Figure 11:
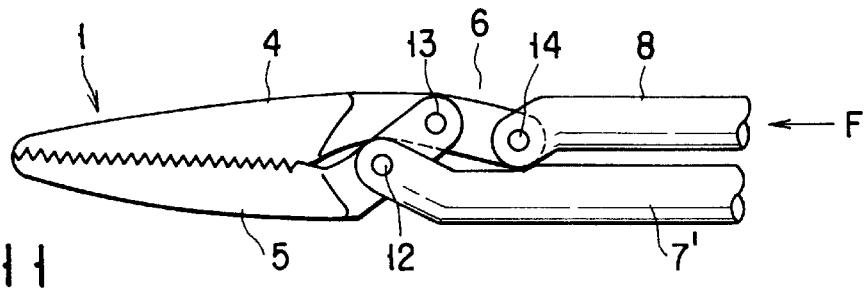
FIG. 11 is a side view of a forceps section of the endoscope forceps of FIG. 10A in a condition of closed jaws.
Figure 12:
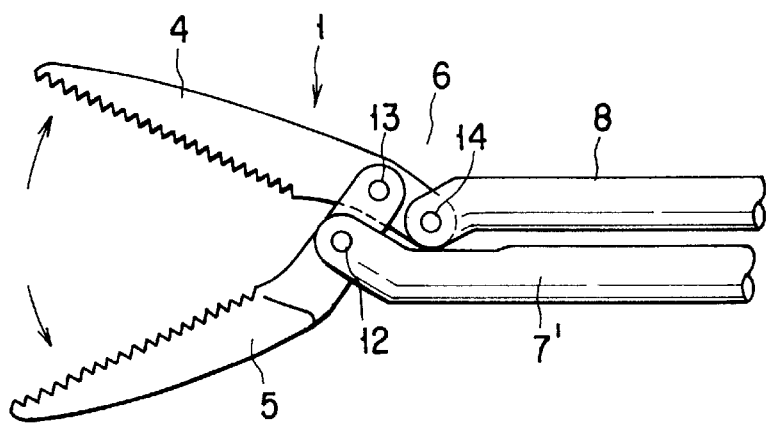
FIG. 12 is a side view of a forceps section of the endoscope forceps of FIG. 10A in a condition of opened jaws.

A first jaw 4 is pivotably mounted at the fore end of an operating rod 8 with a pivotal pin 14 engaging with both. A second jaw 5 is pivotably mounted at the fore end of the stationary rode 7' with a pivotal pin 12 engaging with both. The first and second jaws 4, 5 are pivotably connected with a pivotal pin 13. In a concrete manner, as shown in FIGS. 11 and 12, a slot is formed at the fore end section of the stationary rode 7', the base end portion of the second jaw 5 is fittingly inserted in the slot and the base end is further connected to the stationary rod 7' with a pivotal pin 12 engaging with both. A slot is formed at the fore end section of the operating rod 8 and the base end of the first jaw 4 is fittingly pivotably inserted in the slot with a pivotal pin 14 engaging with both. In addition, a slot is still further formed at the base end section of the second jaw 5 and the base end portion of the first jaw 4 is fittingly inserted in the slot so that the first and second jaws 4, 5 are in a freely pivotable manner connected there with a pivotal pin 13 engaging with both.

A filling tube 16 made of elastic material, such as sillicone rubber which fills a gaps between the insertion section 2 and a trocar, not shown, is disposed between the operating rod 8 and the stationary rod 7'.

The base end section of the stationary rod 7' is mounted to a stationary handle 9a. The base end section of the operating rod 8 is mounted to a pivoting handle 9b with a connecting member 10 interposing therebetween. In a concrete manner, the base end of the connecting member 10 is provided with a engaging section and the engaging section engages with a catching section 9d in the shape of a U letter provided on the head portion of the pivoting handle 9b. The operating rod 8 is allowed to move only along the axial direction by a support mechanism 9c. The support mechanism 9c, which is demountably mounted on the operating rod 8, supports the operating rod 8. When supporting of the operating rod 8 by the support mechanism 9c is released, the operating rod 8 can be pivoted upwardly.

In the above mentioned structure, the operating rod 8 is moved forward or backward by an opening/closing operation of the handles 9 and thereby the first jaw 4 is pivoted. The first jaw 4 moves the base end section of the second jaw 5 while pivoting and thereby the second jaw 5 is pivoted about the pivotal pin 12 at the fore end of the stationary rod 7' as the center. As a result, the first and second jaws 4, 5 are opened or closed (see FIGS. 11 and 12). In a concrete manner, as shown FIG. 11, since a force F in the direction toward the fore end is imposed on the operating rod 8 as shown FIG. 11, the first jaw 4, thereby, receives a force directing to the fore end. The force is transmitted to the second jaw 5 with the help of the pivotal pin 13 and the second jaw 5 pivots about the pivotal pin 12. At this point, since the pivotal pin 13 moves upwardly in company with a pivoting movement of the second jaw 5, the first jaw 4 is forced to pivot about the pivotal pin 14, as the center, located at the fore end of the operating rod 8. In such a manner, the first jaw 4 and the second jaw 5 respectively pivot in opposed directions so as to be spaced apart from each other and as a result, the jaws 4, 5 are opened (see FIG. 12).

When the endoscope forceps of the above mentioned structure is used by being inserting in a trocar, a gap between the operating rod 8 and the stationary rod 7' is filled with the filling tube 16 and a gas in a body cavity is prevented from leakage to the outside.

When the endoscope forceps of the above mentioned structure is disassembled for cleaning, the support mechanism 9c is released and the operating rod 8 is pivoted upwardly. Thereby, the filling tube 16 can be undone and the operating rod 8 and the stationary rod 7' can largely be moved away from each other. Therefore, the operating rod 8 and the stationary rod 7' can be cleaned with the extremity of ease.

The following effects can be obtained, as mentioned above, according to the endoscope forceps of the present embodiment:

(1) a structure is simple;
(2) a spaced-apart condition, which is a condition where the filling tube 16 is undone and thereby the operating rod 8 and the stationary rod 7' are spaced apart form each other, and which makes cleaning easy, can be attained with a simple operation. With application of the spaced-apart condition, structural parts are not disassembled into free parts and thereby there is no fear of any part being in missing during a cleaning operation; and
(3) in the case of an operation in which no pneumoperitoneum is required (that is, otolaryngology, brain surgery, a laparoscopic operation by a suspending method or the like), it is possible to use the endoscope forceps without the filling tube 16.

Figure 13:
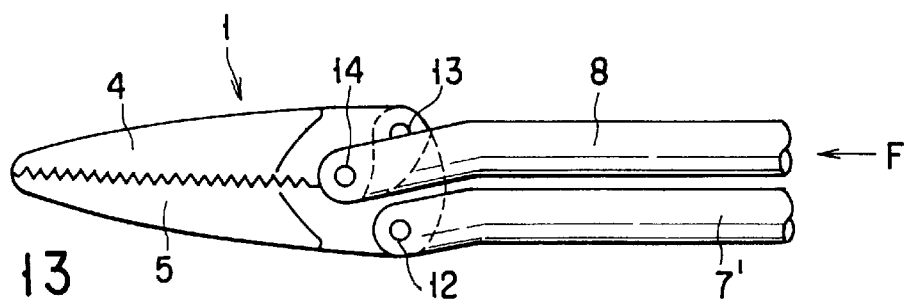
FIG. 13 is a side view of forceps section of an endoscope forceps pertaining to a fourth embodiment of the present invention.
Figure 14:
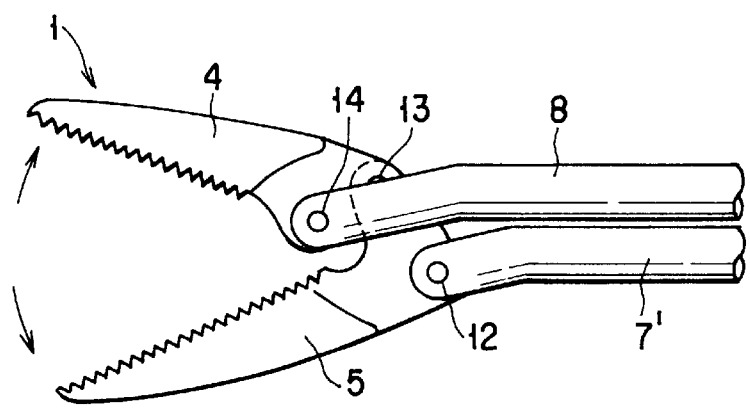
FIG. 14 is a side view of the forceps section of FIG. 13 in a condition of opened jaws.
Figure 15:
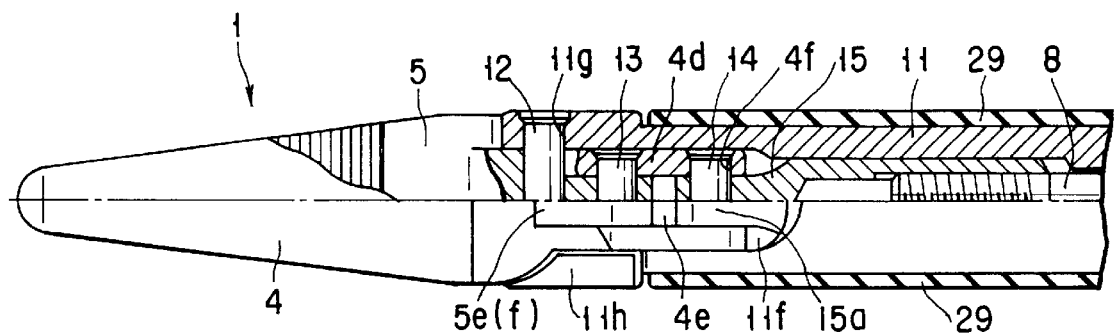
FIG. 15 is a top view partially shown in section of a forceps section of endoscope forceps pertaining to fifth embodiment of the present invention.
Figure 16:
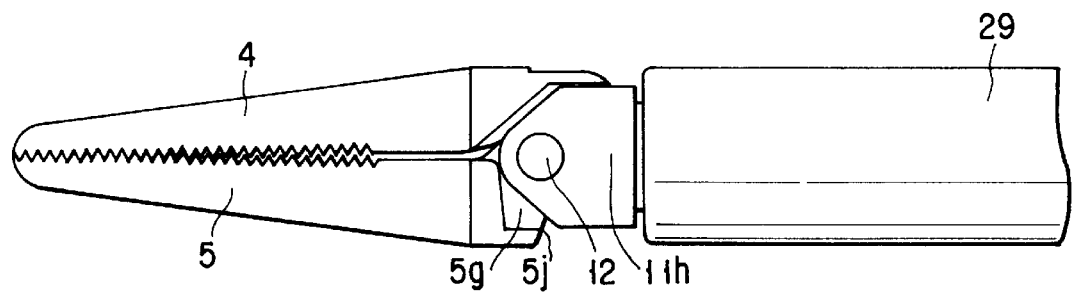
FIG. 16 is a side view of the forceps section of FIG. 15.

FIGS. 13 and 14 show the fourth embodiment of the present invention. The same structural parts as those of the first embodiment are indicated by the same marks in the embodiment and description is omitted thereon.

In the endoscope forceps of the embodiment, the opening/closing mechanism 6 of the third embodiment is improved based on the dynamic principle in the first and second embodiments. In other words, while, in the second embodiment, the support member 11 is connected with the fore end of the sheath 7, in the embodiment a slot is formed at the fore end of a stationary rod 7' and the base end section of the second jaw 5 is fittingly inserted in the slot and pivotably connected to the stationary rod 7'. While, in the second embodiment, the connecting member 15 is provided at the fore end of the operating rode 8, in the embodiment the first jaw 4 is pivotably connected directly to the operating rod 8 at the fore end thereof. A geometrical structure of the opening/closing mechanism 6, other than the direct connection of the first jaw 4 with the operating rod 8, is the same as that of the second embodiment.

Therefore, the endoscope forceps 1 of the embodiment is operable in a similar way to the second embodiment. An inserting section 2 and an operating section 9 are operable in a similar way to that of the third embodiment. Therefore, similar effects to the effects of the first to third embodiments can be obtained.

Positional relations of the three pivotal pins 12, 13, 14 in the first to fourth embodiments will in a concrete manner be described below.

When an X Y coordinate system is set in such a manner that the pivotal pin 14 which is a first pivotal shaft is selected as an origin, X axis is taken along a direction, leftward or rightward, (which is a direction along the axis of the insertion section 2) and Y axis is taken along a direction, upward or downward, (which is a direction perpendicular to X axis), X, Y coordinates of the pins 12, 13, 14 (in a definite way, coordinates of the centers of the respective pins) are set as follows:

coordinates of the pivotal pin 12 are ($\approx$2a, $\approx$-b);
coordinates of the pivotal pin 13 are (a, b); and
coordinates of the pivotal pin 14 are (0, 0).

However, in FIG. 5, there must be $\theta = \tan^{-1} (b/a) \approx 60° > 45°$ and therefore, $b/a \approx \sqrt{3} = 1.73$ or $b/a > 1$. This relation between numerical values a and b is the similar in the following embodiments. Actually, if the diameter of an insertion section is set 5 mm, a=0.7 to 0.8 mm, b=1.2 to 1.4 mm and 2a=1.4 to 1.6 mm.

Concrete examples of coordinates of the pins 12, 13, 13 satisfying the above condition will be shown for each embodiment:

in the case of the first embodiment, coordinates of the pivotal pin 14 are (0, 0), coordinates of the pivotal pin 13 are (0.8, 1.3) and coordinates of the pivotal pin 12 are (1.4, −1.5);

in the cases of the second and third embodiments, coordinates of the pivotal pin 14 are (0, 0), coordinates of the pivotal pin 13 are (1, 1.4) and coordinates of the pivotal pin 12 are (1.6, −1.4).

In the two examples, proper design values are given as double-opening forceps with jaws opened/closed upwardly and downwardly with almost equal movements. If values close to the examples are selected, the grasping force f described in the first embodiment can be produced.

When the following sets of coordinates are selected, similar effects to the effects obtained in the cases of the above mentioned set values can be obtained:

coordinates of the pivotal pin 14 are (0, 0); coordinates of the pivotal pin 13 are (a, 2b); and coordinates of the pivotal pin 12 are (2a, 0).

A set of coordinates in which partners for coupling at the pivotal pins 12, 14 are exchanged can also be set:

coordinates of the pivotal pin 12 are (−2a, b); coordinates of the pivotal pin 13 are (−a, 2b); and coordinates of the pivotal pin 14 are (0, 0).

In addition, an example of a set of coordinates for the third embodiment is shown as follows:

coordinates of the pivotal pin 12 are (−2b, 0);

coordinates of the pivotal pin 13 are (−b, a); and coordinates of the pivotal pin 14 are (0, 0).

According to the set of coordinates for the third embodiment, the grasping force f, which is produced at the fore end, is close to a value shown in the conventional example of FIG. 34, which is different from the cases of the first, second and fourth embodiments.

FIGS. 15 to 18 show the fifth embodiment of the present invention. In the embodiment, the stationary rod 7' and the operating rod 8, which are two rods, in the third embodiments, are respectively changed with a tubular sheath 7, an operating rod 8 and a support member 11 as in the first embodiment. Since two rods parallel to each other are used in the third embodiment, forces acting on the two rods are respectively directed in the opposed directions when the handles 9 are operated, which is resulted in that the insertion section 2 is subject to bending. The embodiment provides an endoscope forceps to solve such a problem.

As shown in FIGS. 15 through 18, the base end section 4*d* of a first jaw 4 constituting a forceps section 1 has a slot 4*e* and the base end 4*d* assumes a structure of two divided parts. A first engaging section 5*f* with a thickness to be fittingly inserted in the gap of the slot 4*e* of the first jaw 4 is formed in the base end section 5*e* of the second jaw 5 and is engaged in the slot 4*e*. Besides, the first engaging section 5*f* is in a freely pivotable manner connected to the base end section (a portion with a structure of two divided parts) 4*d* of the first jaw 4 where the slot 4*e* is formed with a pivotal pin 13 engaging with both.

A second engaging section 5*g* is formed in the base end section 5*e* of the second jaw 5 at a position closer to the fore end of the second jaw 5 than the first engaging section 5*f*. A slot 11*f* and a pivotal hole 11*g* are formed in a support section 11*h*, in an expanding manner, provided at the fore end side of a support member 11. The second engaging section 5*g* has a thickness which fits a width of the slot 11*f* of the support member 11 and not only fittingly inserted in the slot 11*f* but also in a freely pivotable manner mounted to the support section 11*h* with a pivotal pin 12 engaging with both.

A tubular sheath 7 is connected with the base end of the support member 11. A portion of the support member 11 which is extended closer to the base end than the support section 11*h* is covered with an insulating tube 29 on its outer surface. The support section 11*h* of the support member 11 assumes a cylinder and the outer diameter thereof is set so as to be equal to that of the insulating tube 29. The insulating tube 29, as in the first and second embodiments, covers a great part of the support member 11 and the fore end thereof approaches a point close to the first and second jaws 4, 5.

A pivotal hole 4*f* is formed in the base end section 4*d* of the first jaw 4. In the pivotal hole 4*f*, inserted is a pivotal pin 14 which pivotably connects the fore end section 15*a* of a connecting member 15 mounted at the fore end of the operating rod 8 and the first jaw 4. The fore end section 15*a* of the connecting member 15 has the shape of a flat plate and is fittingly inserted in the slot 4*e* of the base end section 4*d* of the first jaw 4.

Positional relations between the pivotal pins 12, 13, 14 are almost similar to those in the third embodiment. The pivotal pins 12, 13, 14 form a triangle and a distance of the pivotal pins 12 and 14 is set to be longer. An angle between a straight line connecting the centers of the pivotal pins 13 and 12, and a straight line connecting the centers of the pivotal pins 13 and 14 is set to be an obtuse angle. While, in the third embodiment, coordinates of the center of the pivotal pin 12 are set to be (≈−2b, 0), in the embodiment coordinates of the center of the pivotal pin 12 are set to be (≈−2b, c). Herein, a relation between numerical values a and c is a>c≧0. In this case, a way to produce a grasping force at the fore end of jaws are different form the way in the first embodiment and the maximal force is produced in a condition that the first second jaws 4, 5 are perfectly opened and to the contrary the minimal force is produced in a condition that the first second jaws 4, 5 are perfectly closed. But this trend is not so much extreme. This is a similar trend to the way to produce a force in the third embodiment.

Then, an operation of the endoscope forceps having the above mentioned structure will be described.

When handles 9 are opened/closed, the operating rod 8 is moved, forward or backward, and thereby the first jaw 4 is forced to pivot. The first jaw 4 moves the base end section of the second jaw 5 while pivoting itself and thereby the second jaw 5 is forced to pivot about the pivotal pin 12 as the center. As a result, the first and second jaws 4, 5 perform opening/closing movements.

Figure 17:
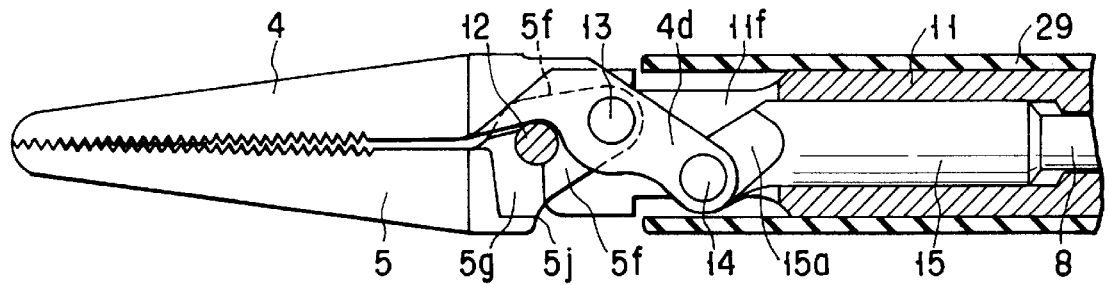
FIG. 17 is a sectional side view of the forceps section of FIG. 15 in a condition of closed jaws.

FIG. 17 shows a condition where the operating rod 8 is pulled (toward the handles 9) and the first and second jaws 4, 5 are perfectly closed. The base end sections of the first and second jaws 4, 5 work as links but they are confined inside the outer diameter of the insulating tube 29 in a condition of perfectly closed jaws as shown in the figure. Movements in closing directions of the first and second jaws 4, 5 are terminated when both fore ends come to be in contact with each other.

Figure 18:
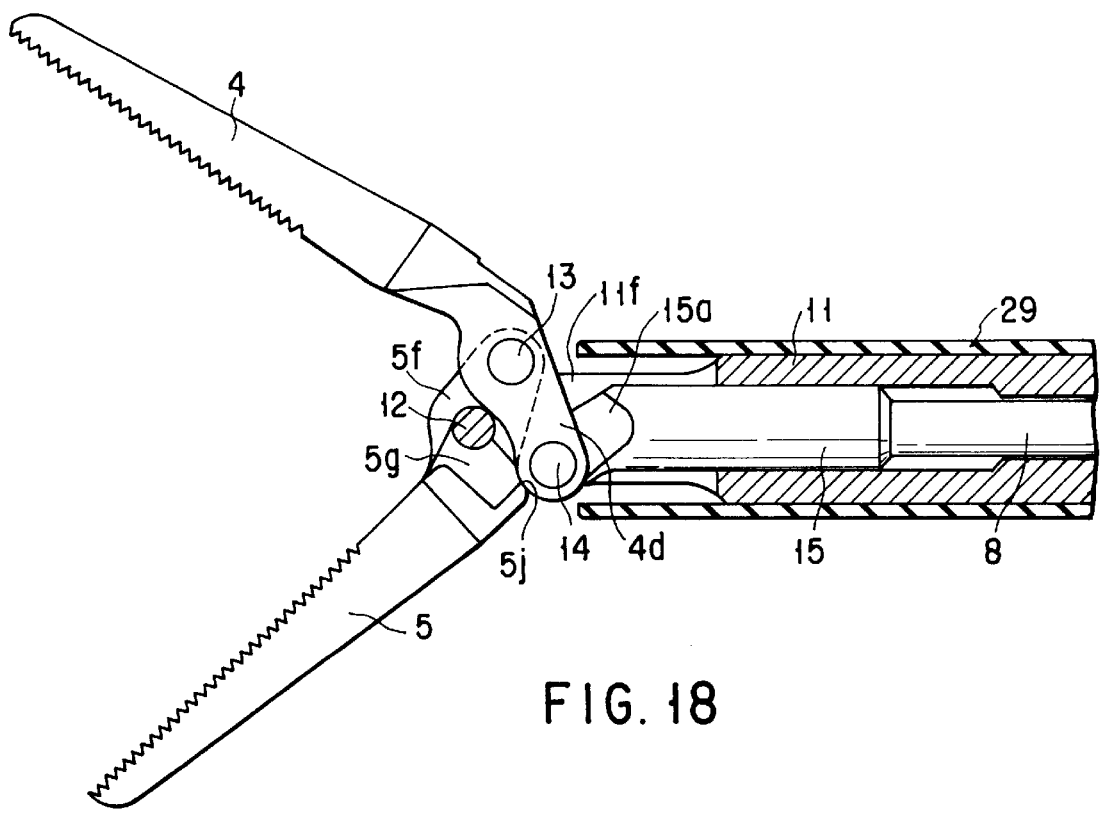
FIG. 18 is a sectional side view of the forceps section of FIG. 15 in a condition of opened jaws.

FIG. 18 shows a condition where the operating rod 8 is pushed toward the fore end and the first and second jaws 4, 5 are perfectly opened. The base end sections of the first and second jaws 4, 5 protrude outside the outer diameter of the insulating tube, and at the same time they move forward or toward the fore ends, as shown in the figure. Therefore, it is avoided the a brim of the fore end of the insulating tube 29 and the base end sections of the first and second jaws 4, 5 interferes in one another. Movements of the first and second jaws 4, 5 in opening directions are stopped when the base end section 4*d* of the first jaw 4 and a step portion 5*j* at the base end section of the second jaw 5 come to be in contact with each other.

According to the endoscope forceps of the present invention, as mentioned above, the following effects can be obtained:

(1) when a tissue like a membrane is to be torn off in the vicinity of a condition of perfect opening of the first and second jaws, a finely controlled tearing-off can be assured since a force to be produced is large and a operating range of the operating section 3 is wide;

(2) since the first and second jaws 4, 5 can be opened/closed without use of an intermediate link only to be used for simply transmitting a force as in the quadric crank chain shown in FIG. 34 a structure is simple, excellent in strength and reliability and low in cost;

(3) while a opening/closing mechanism is provided at a position closer to the base ends than the pivotal shaft 12 between the first and second jaws 4, 5 and the support member 11, a great part of the base end portions of the first and second jaws 4, 5 can be covered with an insulating material, since there is no interference between the opening/closing mechanism and the insulating tube 29, whereby high electrical safety can be attained; and (4) since there is no protrusion of structural elements of the forceps section 1 outside the outer diameter of the insertion section 2 by opening/closing operations of the first and second jaws 4, 5, there is no fear to burn other organs than a target organ in cauterization by means of high frequency heating and simultaneously there is no chance where a suture thread catches a structural element of the forceps section 1 when a suture operation is conducted with the jaws grasping a suture thread, which makes ligation in a body cavity easy.

FIGS. 19 through 24 shows the sixth embodiment of the present invention. Structural parts of the embodiment, which are also used in the above mentioned ones, are indicated by the same marks and description thereon is omitted.

As shown in FIGS. 19 through 22, an endoscope forceps of the embodiment comprises: a first and second jaws 51, 52 for grasping and tearing-off; an actuating member 57 which is connected to an operating rod 8, and which transmits an operating force of handles 9 to the jaws 51, 52; and a support member 53 to support the actuating member 57.

Figure 21:
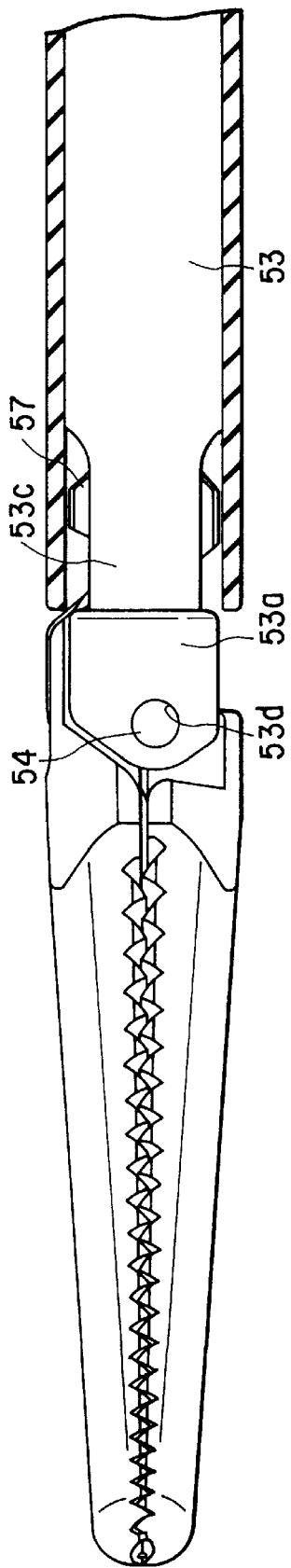
FIG. 21 is a side view of the forceps section of FIG. 19.
Figure 22:
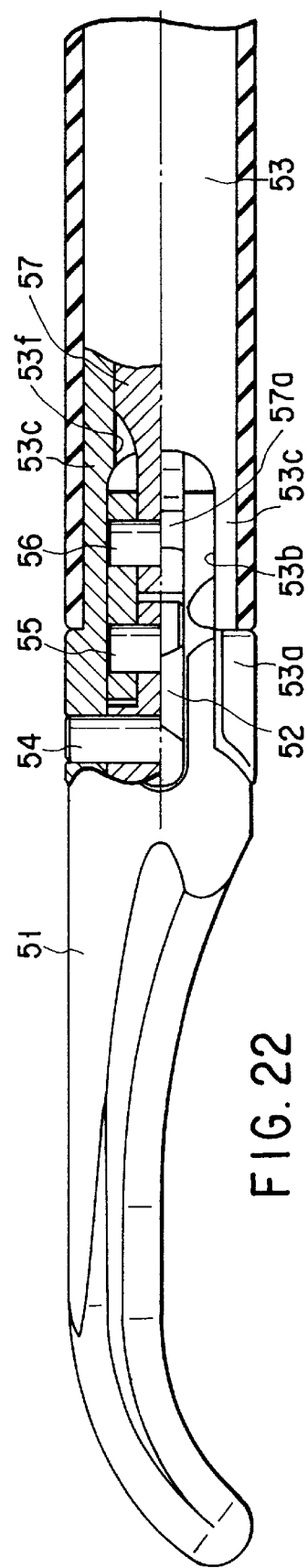
FIG. 22 is a top view of the forceps section of FIG. 19.

As in a detailed manner shown in FIGS. 21 and 22, the support member 53 is constructed from an expanding fore end section 53a extending forward from the fore end of a sheath 7; a pair of arm sections 53c, 53c extending toward the base end side from the expanding fore end section 53a; a slot section 53b which is formed between the arm sections 53c, 53c, and which supports the jaws 51, 52 in a sandwiching manner; a pivotal hole 53d through which a pivotal pin 54 is inserted, the pivotal pin 54 pivotably connecting the support member 53 and the second jaw 52; and a hole 53f through which the actuating member 57 is fittingly inserted. Both ends of the pivotal pin 54 is fixed to the support member 53 by welding or the like.

Figure 19:
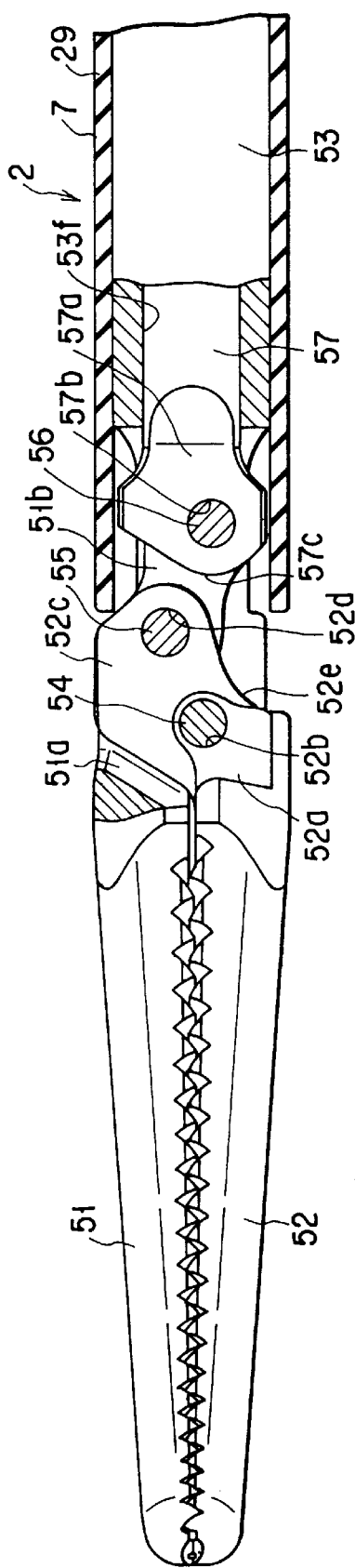
FIG. 19 is a view in a section including a central line of a forceps section of an endoscope forceps pertaining to a sixth embodiment of the present invention.
Figure 20:
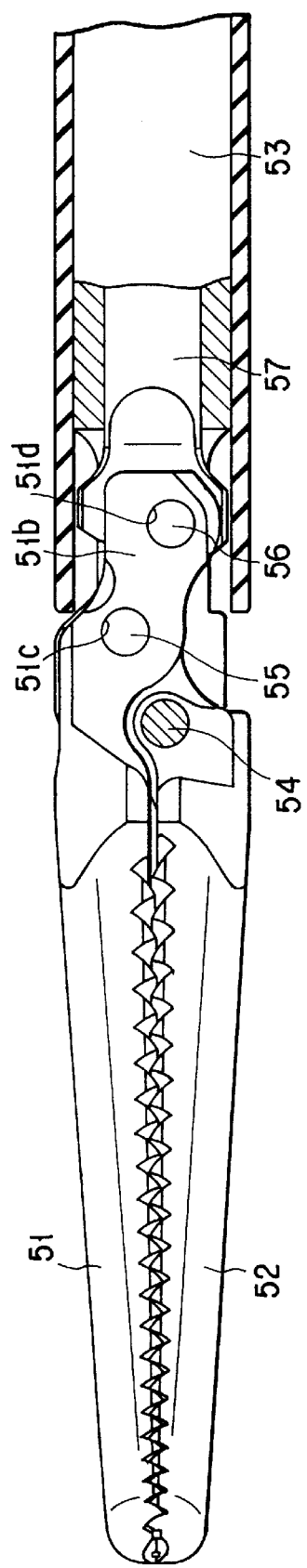
FIG. 20 is a view in a section including a parallel line offset from the central line of the forceps section of FIG. 19.

As in a detailed manner shown in FIGS. 19 and 20, the first jaw 51 has a pair of arm sections 51b, 51b in the base end side. A slot 51a is formed between the pair of arm sections 51b, 51b. The first jaw 51 has a pivotal hole 51c through which a pivotal pin 55 for pivotably connecting the first jaw 51 and second jaw 52 is inserted and a pivotal hole 51d through which a pivotal pin 56 for pivotably connecting the first jaw 51 and the fore end section of the actuating member 57 is inserted. The pivotal pins 55, 56 are not fixed at any of the first and second jaws 51, 52.

Figure 23:
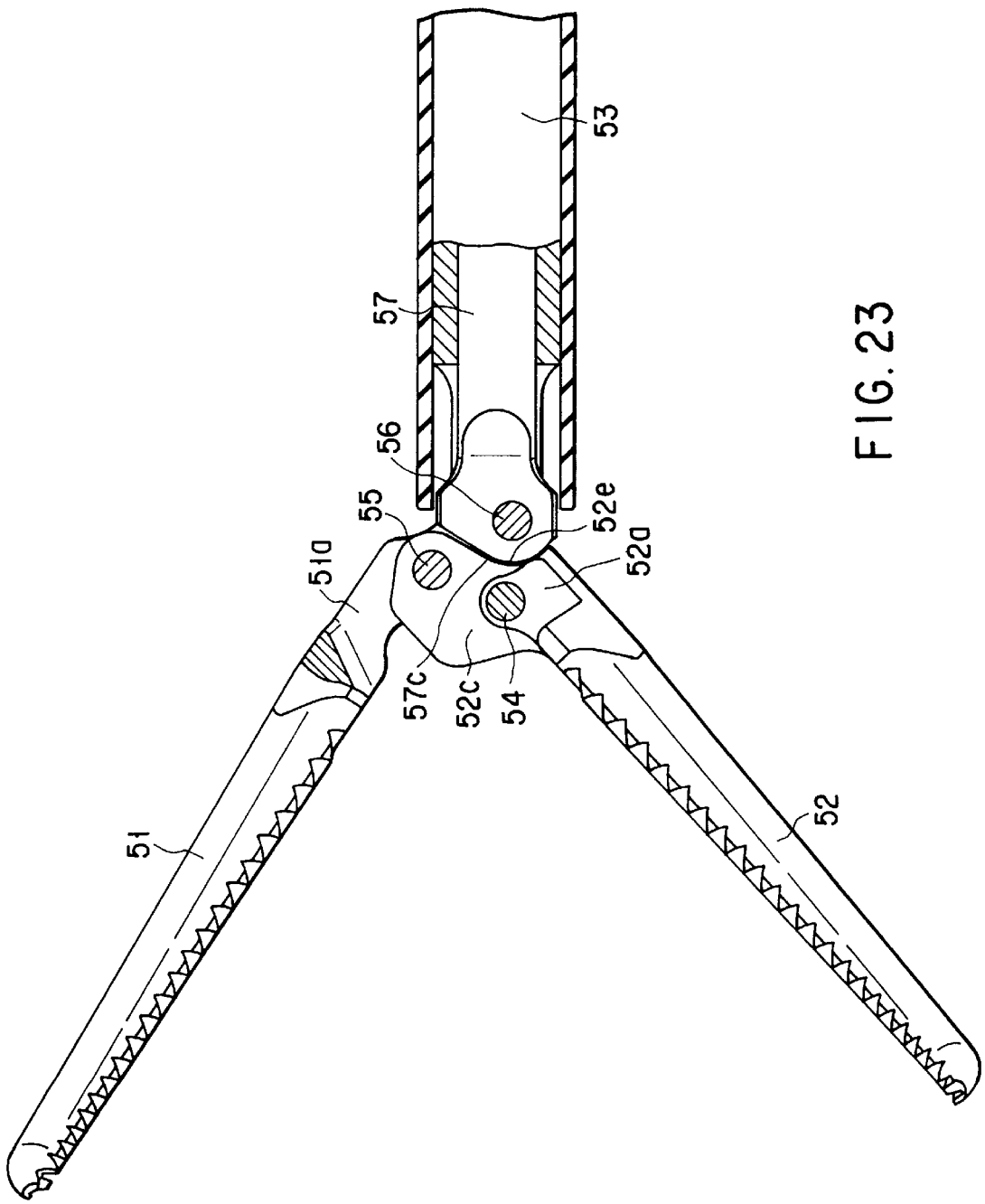
FIG. 23 is a view in a section including the central line of the forceps section of FIG. 19 in a condition of perfectly opened jaws.
Figure 24:
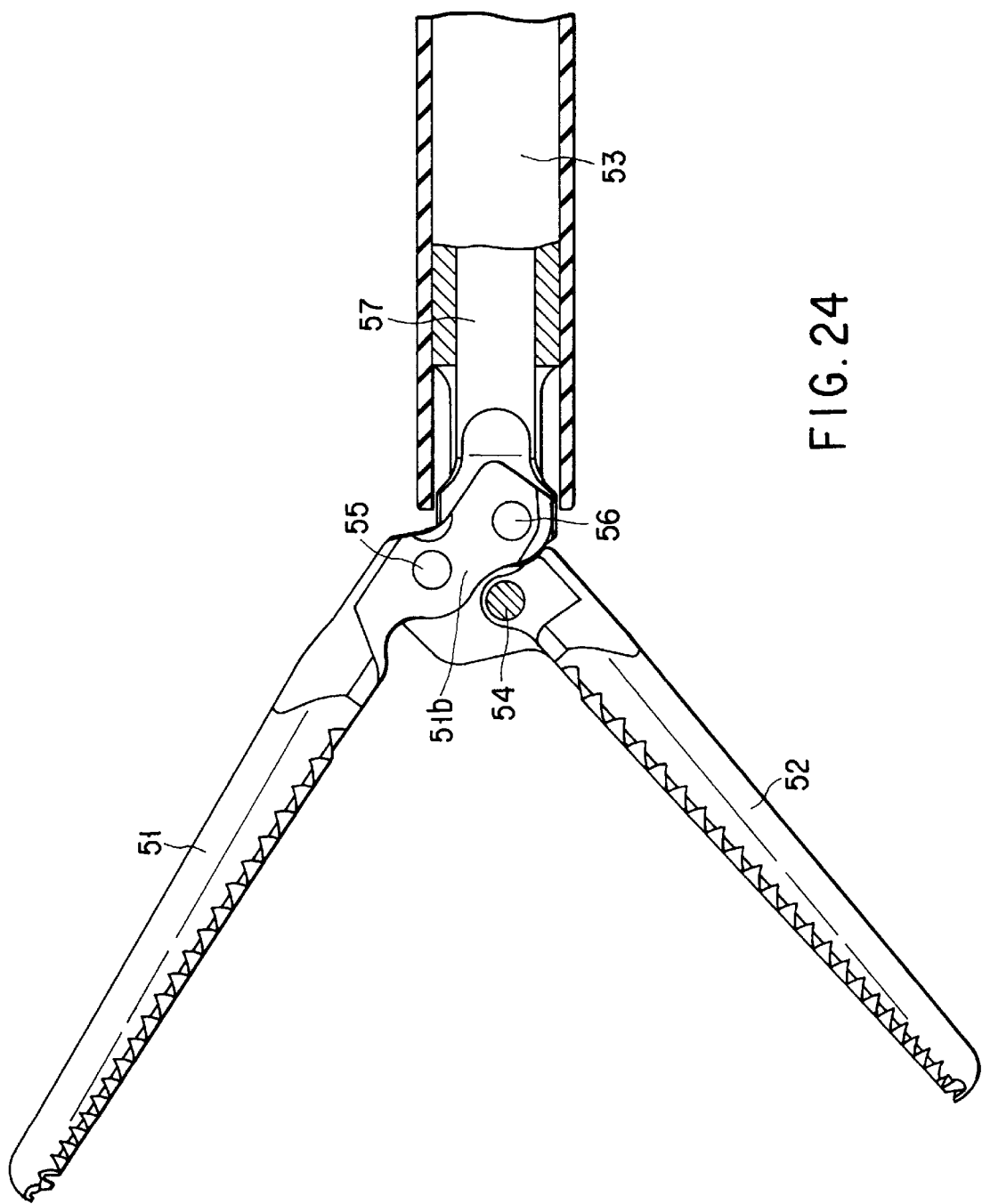
FIG. 24 is a view in a section including a parallel line offset from the central line of the forceps section of FIG. 19 in a condition of perfectly opened jaws.

The second jaw 52 comprises: a first engaging section 52a which is fittingly inserted in the slot section 53b of the support member 53; a pivotal hole 52b through which a pivotal pin 54 is inserted; a second engaging section 52c which is fittingly inserted in the slot 51a of the first jaw 51; a pivotal hole 52d through which a pivotal pin 55 is inserted; and a contacting section 52e which contacts with a contacting section 57c, described later, of the actuating member 57 when the jaws 51, 52 are perfectly opened (see FIG. 23).

The actuating member 57 comprises: a flat section 57a fittingly inserted in the slot section 51a of the first jaw 51; a pivotal hole 57b through which a pivotal pin 56 is inserted; and the contacting section 57c contacting with the contacting section 52e of the second jaw 52 when the jaws 51, 52 are perfectly opened.

When an X Y coordinate system is set, the system comprising: an origin of the pivotal pin 56; X axis which extends along a direction side to side in the figure, that is along the axial direction of the insertion section 2; and Y axis which extends along a direction, above to below, that is along a direction perpendicular to X axis, coordinates of the pivotal pins 54, 55, 56 (in a definite manner, the coordinates of the centers of the pins) are set as follows in a condition where the first and second jaws 51, 52 are perfectly closed: coordinates of the pivotal pin 54 are ($\approx$−2b, $\approx$c), coordinates of the pivotal pin 55 are (−b, a) and coordinates of the pivotal pin 56 are (0, 0), wherein a>b$\geq$0.

While, in the fifth embodiment, the position of the pivotal pin 12 which pivotably connects the support 11 and the second jaw 5 coincides with the central axis of the insertion section 2, in the embodiment the pivotal pin 54 which pivotably connects the support member 53 and the second jaw 52 is positioned slightly lower than the central axis of the insertion section 2.

Therefore, according to the above mentioned structure, the jaws 51, 52 are opened or closed in a similar way to that in the fifth embodiment. In other words, when the handles 9 are operated, the operating rod 8 and the actuating member 57 are moved forward or backward, thereby the pivotal pins 55, 56 are in turn moved and as a result, the jaws 51, 52 are opened or closed. In this case, when the contacting sections 52e, 57c contact with each other, a opening movement is limited (see FIGS. 23 and 24). When the fore ends of the jaws 51, 52 contact with each other, a closing movement is limited.

As mentioned above, with use of an endoscope forceps of the embodiment, a similar effect to that in the fifth embodiment can be attained. A strength of the arm sections 51b of the first jaw 51 passing over the pivotal pin 54 located at the closest position to the fore end is increased.

FIGS. 25 through 28 show the seventh embodiment of the present invention. Structural parts of the embodiment, which are also used in the sixth embodiment, are indicated by the same marks and description thereon is omitted.

As shown in FIGS. 25 and 26, an endoscope forceps of the embodiment comprises; first and second jaws 58, 52 for grasping and tearing-off; an actuating member 59, which is connected to an operating rod 8, and which transmits an operating force of handles 9 to the jaws 58, 52; and a support member 53 to support the jaws 58, 52 and the actuating member 59.

The first jaw 58 comprises a pair of arm sections 58b, 58b formed in the base end side. A slot 58a, through which an engaging section 52c of the second jaw 52 is fittingly inserted, is formed between the arm sections 58b, 58b. A pivotal hole 58c through which a pivotal pin 55 is inserted and a pivotal hole 58d through which a pivotal pin 56 are formed in the first jaw 58.

Figure 27:
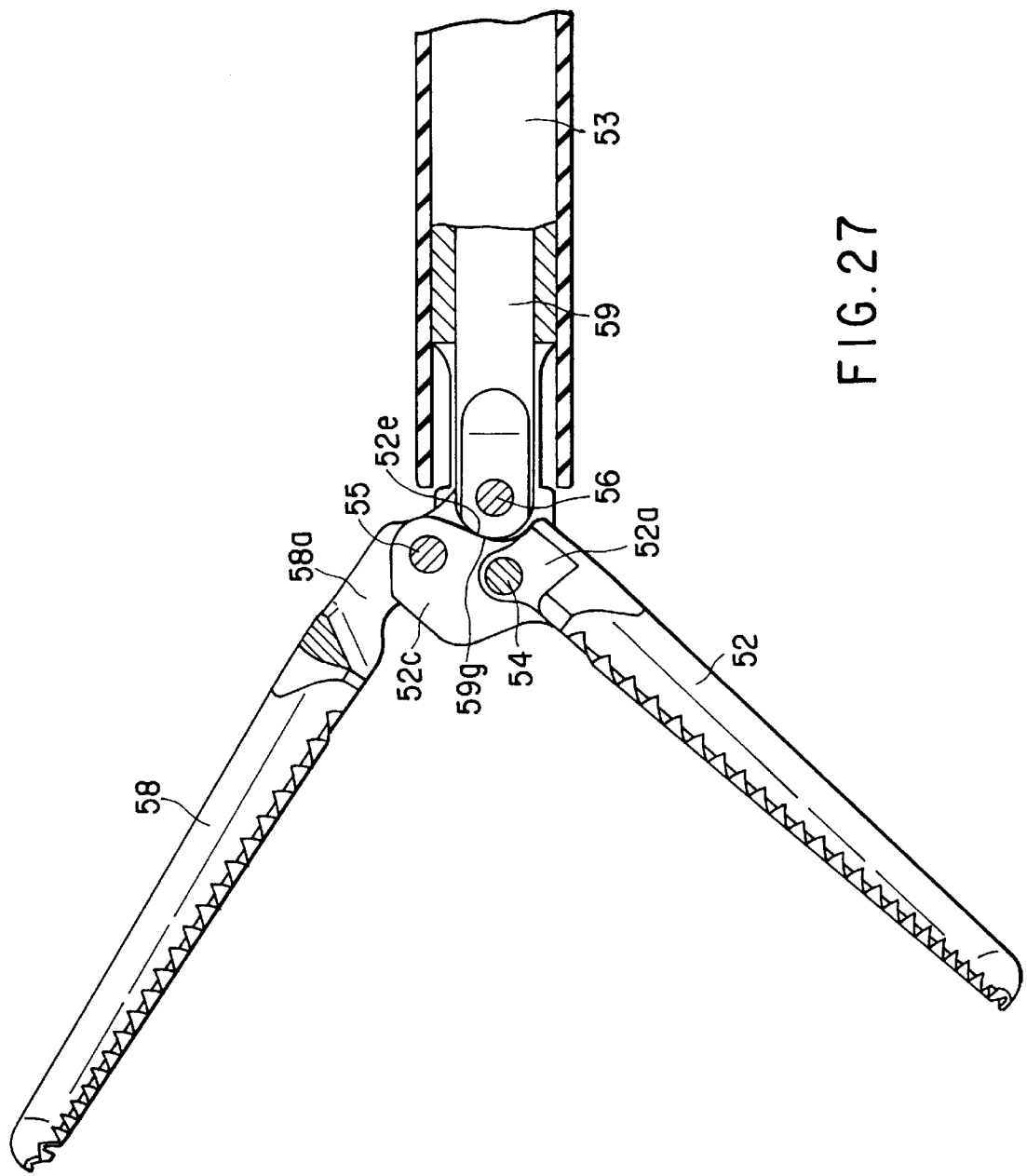
FIG. 27 is a view in a section including the central line of the forceps section of FIG. 25 in a condition of perfectly opened jaws.
Figure 28:
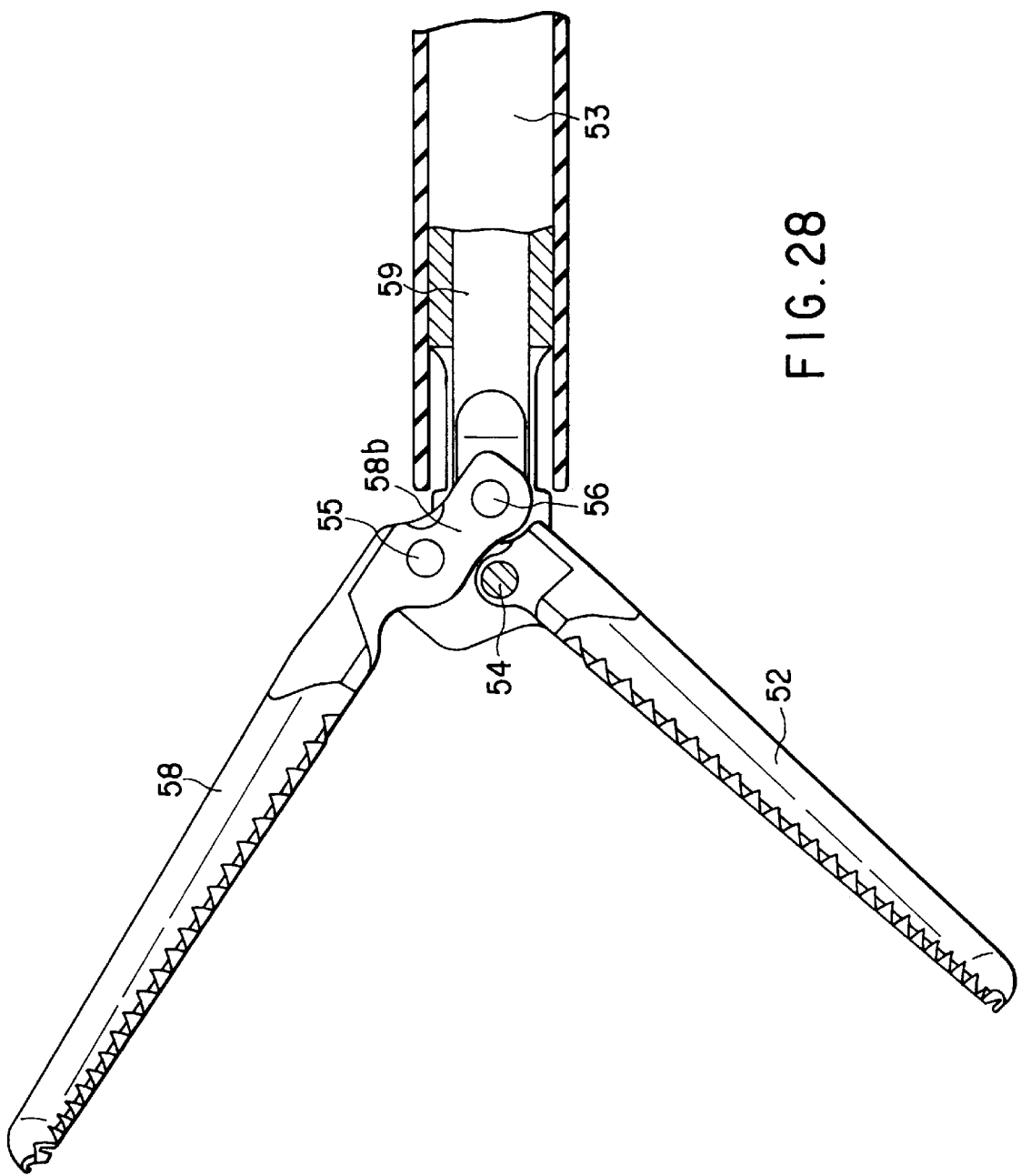
FIG. 28 is a view in a section including a parallel line offset from the central line of the forceps section of FIG. 25 in a condition of perfectly opened jaws.

The actuating member 59 comprises: a flat section 59e to be fittingly inserted in the slot section 58a of the first jaw 58; a pivotal hole 59f through which the pivotal pin 56 is inserted; and a contacting section 59e to contact with a contacting section 52e of the second jaw 52 when the jaws 58, 52 are perfectly opened (see FIGS. 27 and 28).

When an X Y coordinate system is set, the system comprising: an origin of the pivotal pin 56; X axis which extends along a direction side to side in the figure, that is along the axial direction of the insertion section 2; and Y axis which extends along a direction, above to below, that is along a direction perpendicular to X axis, coordinates of the pivotal pins 54, 55, 56 (in a definite manner, the coordinates of the centers of the pins) are set as follows in a condition where the first and second jaws 58, 52 are perfectly closed: coordinates of the pivotal pin 54 are (≈-2b, ≈-c), coordinates of the pivotal pin 55 are (-b, a) and coordinates of the pivotal pin 56 are (0, 0), wherein a>c≧0.

While, in the sixth embodiment, the pivotal pin 56 is located slightly lower than the central axis of the inserting section 2, in the embodiment the pivotal pin 56 coincides with the central axis of the insertion axis 2. Even when the pivotal pin 56 coincides with the central axis of the insertion section 2 in such a manner, positions of the jaws 58, 52 are almost the same as those of the sixth embodiment in conditions of not only perfectly opened jaws but perfectly closed jaws. Therefore, there arises no problem in use of an practical phase.

With use of the above mentioned structure, the jaws 58, 52 are opened and closed in an almost similar manner to the fifth embodiment. Since the structure is different from the sixth embodiment in that the shape of the fore end of the actuating member 59 assumes a rod and therefore the structure is simple and the production cost can also be reduced.

FIGS. 29 to 33 show the eighth embodiment of the present invention. Structural parts of the embodiment, which are also used in the above mentioned embodiments, are indicated by the same marks and description thereon is omitted.

Figure 29:
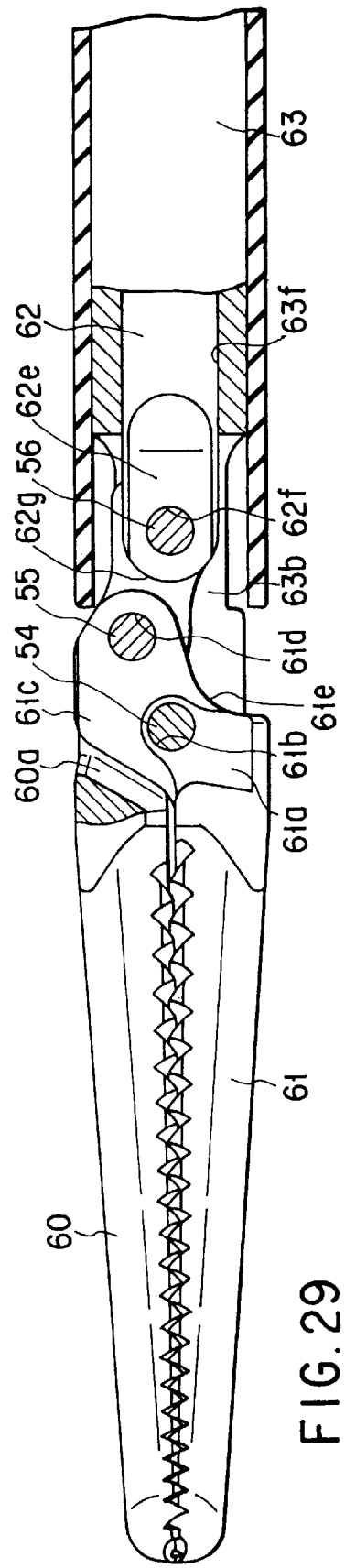
FIG. 29 is a view in a section including a central line of a forceps section of an endoscope forceps pertaining to an eighth embodiment of the present invention.
Figure 31:
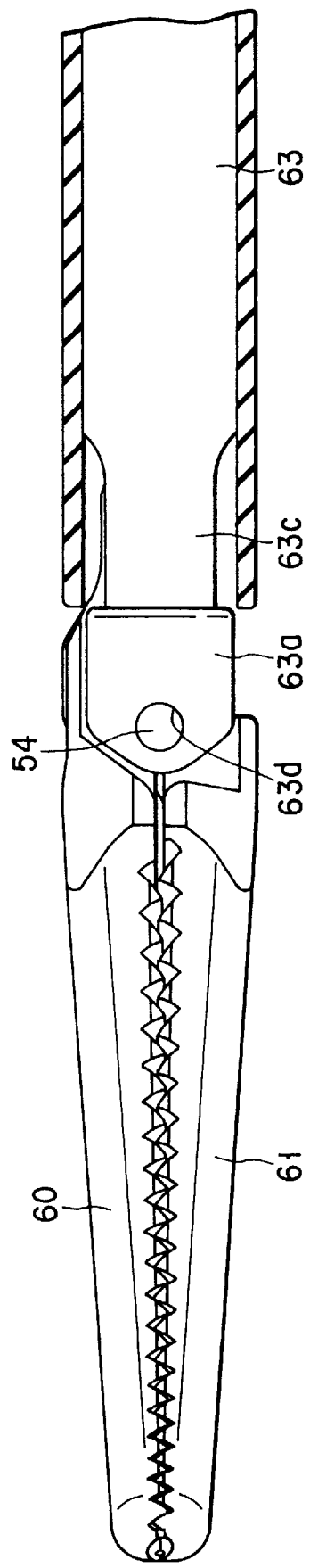
FIG. 31 is a side view of the forceps section of FIG. 29.

As shown in FIGS. 29 and 31, an endoscope forceps of the embodiment comprises; first and second jaws 60, 61 for grasping and tearing-off; an actuating member 62, which is connected to an operating rod 8, and which transmits an operating force of handles 9 to the jaws 60, 61; and a support member 63 to support the jaws 60, 61 and the actuating member 62.

As in a detailed manner shown in FIG. 31, the support member 63 is constructed from an expanding fore end section 63a extending forward from the fore end of a sheath 7; a pair of arm sections 63c, 63c extending toward the base end side from the expanding fore end section 63b; a slot section 63b which is formed between the arm sections 63c, 63c, and which supports the jaws 60, 61 in a sandwiching manner (see FIGS. 29 and 30); a pivotal hole 63d through which a pivotal pin 54 is inserted, the pivotal pin 54 pivotably connecting the support member 63 and the second jaw 61; and a hole 63f through which the actuating member 62 is fittingly inserted. Both ends of the pivotal pin 54 is fixed to the support member 63 by welding or the like.

Figure 30:
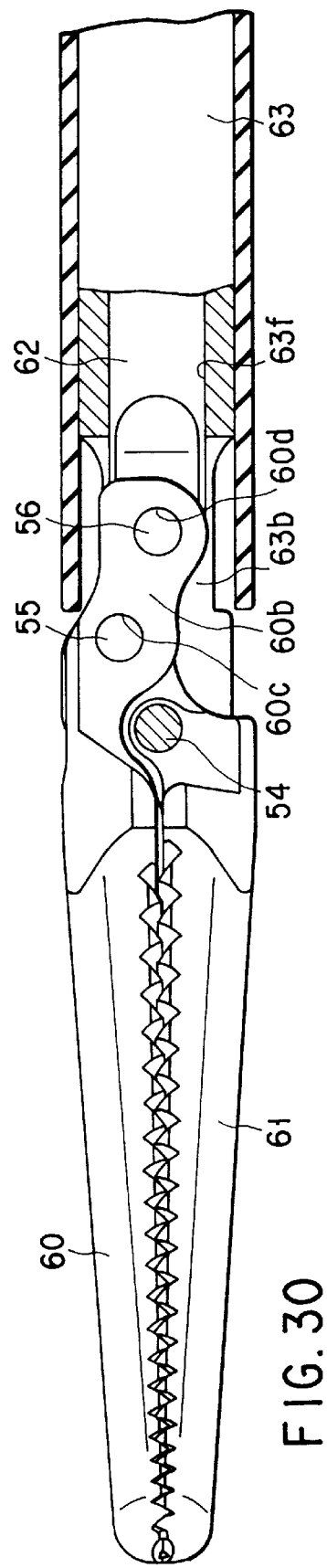
FIG. 30 is a view in a section including a parallel line offset from the central line of the forceps section of FIG. 29.

As in a detailed manner shown in FIGS. 29 and 30, the first jaw 60 has a pair of arm sections 60b, 60b in the base end side. A slot 60a is formed between the pair of arm sections 60b, 60b. The first jaw 60 has a pivotal hole 60c through which a pivotal pin 55 for pivotably connecting the first jaw 60 and second jaw 61 is inserted and a pivotal hole 60d through which a pivotal pin 56 for pivotably connecting the first jaw 60 and the fore end section of the actuating member 62 is inserted. The pivotal pins 55, 56 are not fixed at any of the first and second jaws 60, 61.

Figure 32:
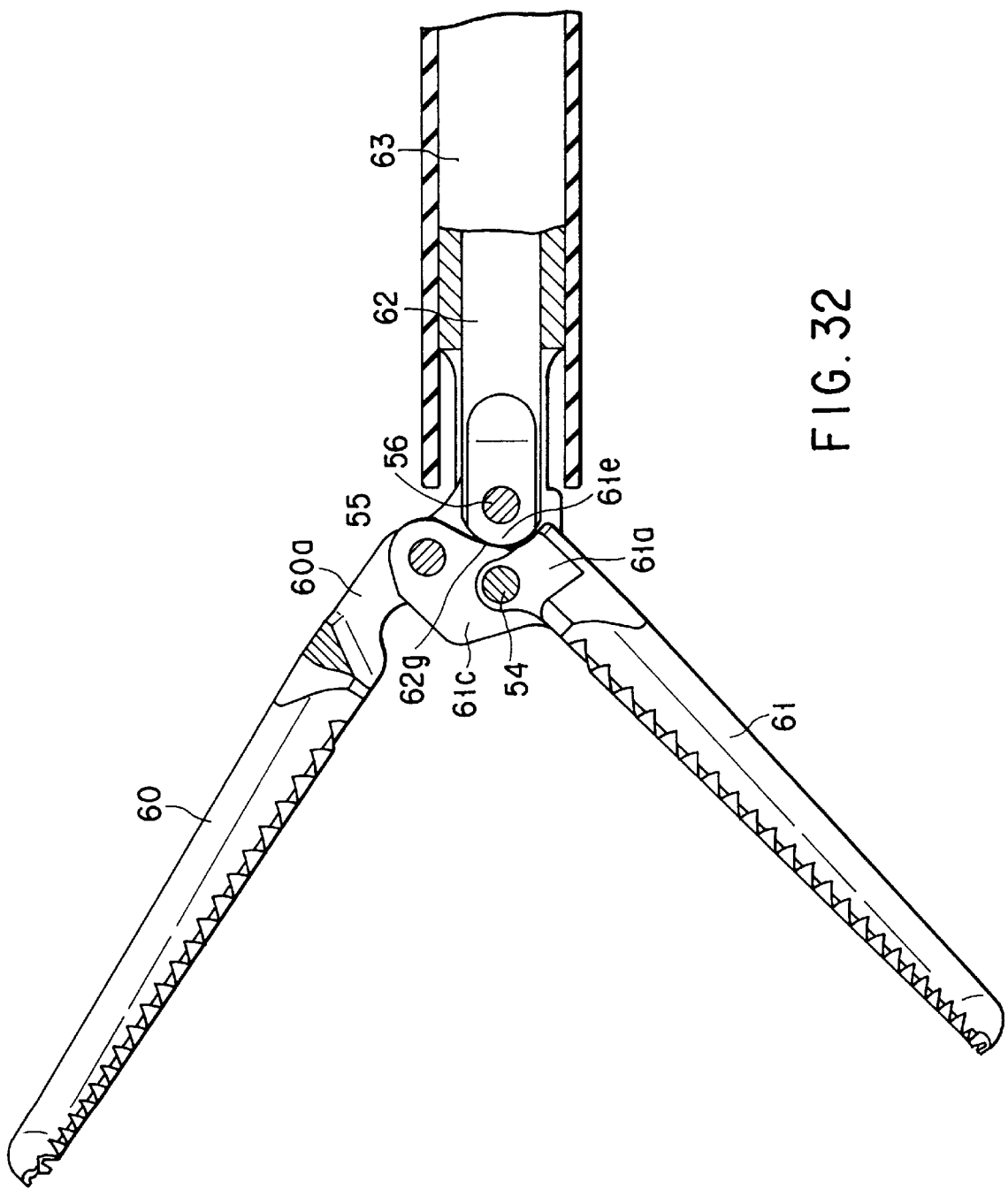
FIG. 32 is a view in a section including the central line of the forceps section of FIG. 29 in a condition of perfectly opened jaws.
Figure 33:
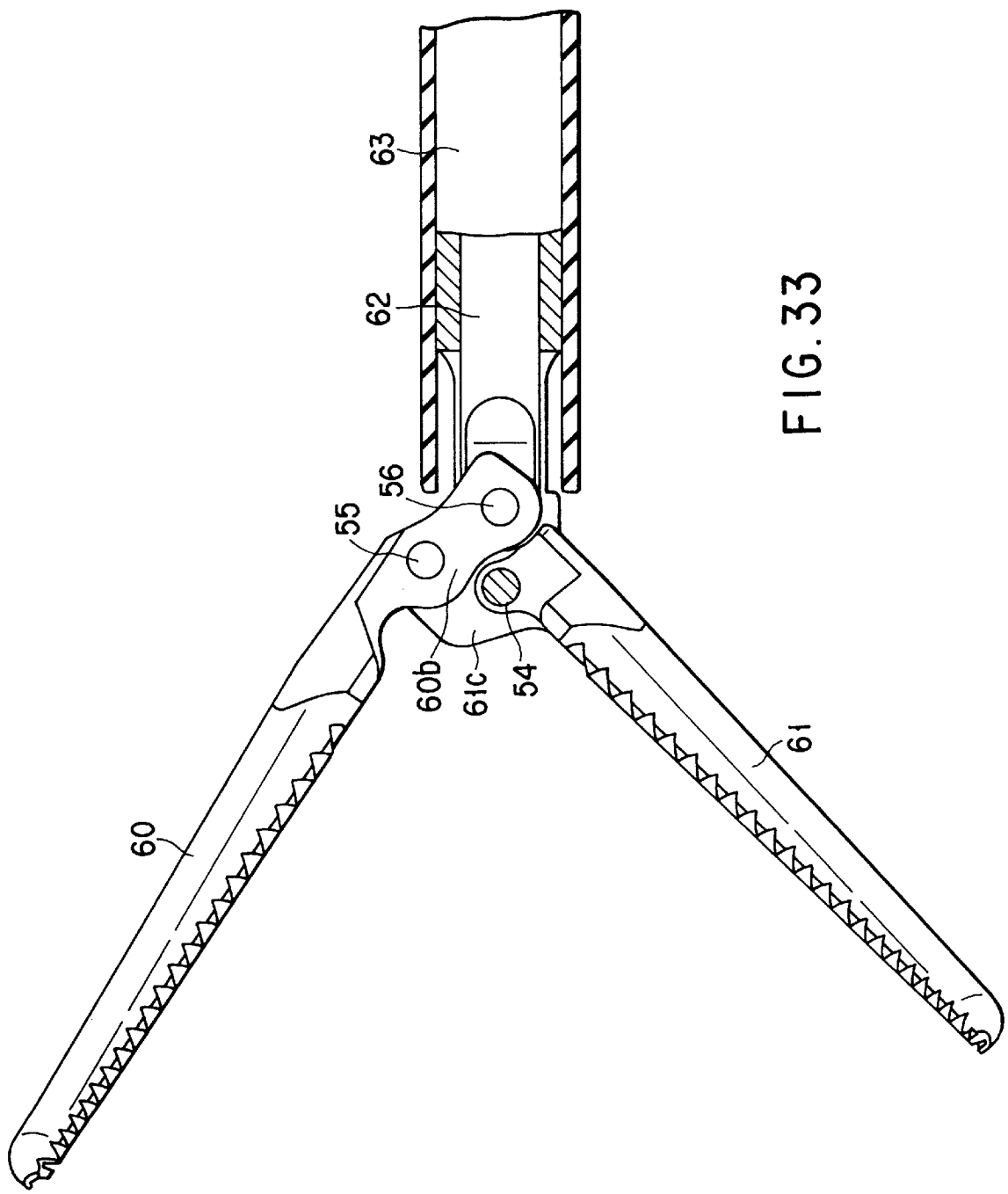
FIG. 33 is a view in a section including a parallel line offset from the central line of the forceps section of FIG. 29 in a condition of perfectly opened jaws.

The second jaw 61 comprises: a first engaging section 61a which is fittingly inserted in the slot section 63b of the support member 63, a pivotal hole 61b through which a pivotal pin 54 is inserted; a second engaging section 61c which is fittingly inserted in the slot 60a of the first jaw 60; a pivotal hole 61d through which a pivotal pin 55 is inserted; a contacting section 61e which contacts with a contacting section 62g, described later, of the actuating member 62 when the jaws 60, 61 are perfectly opened (see FIG. 32).

The actuating member 62 comprises: a flat section 62e fittingly inserted in the slot section 60a of the first jaw 60; a pivotal hole 62f through which a pivotal pin 56 is inserted; and the contacting section 62g contacting with the contacting section 61e of the second jaw 61 when the jaws 60, 61 are perfectly opened.

When an X Y coordinate system is set, the system comprising: an origin of the pivotal pin 56; X axis which extends along a direction, side to side, in the figure, that is along the axial direction of the insertion section 2; and Y axis which extends along a direction, above to below, that is along a direction perpendicular to X axis, coordinates of the pivotal pins 54, 55, 56 (in a definite manner, the coordinates of the centers of the pins) are set as follows in a condition where the first and second jaws 60, 61 are perfectly closed: coordinates of the pivotal pin 54 are (-2b, 0), coordinates of the pivotal pin 55 are (-b, a) and coordinates of the pivotal pin 56 are (0, 0), wherein a>0.

While, in the sixth embodiment, the pivotal pin 54 is located slightly lower than the central axis of the insertion section 2, in the embodiment the pivotal pin 54 coincides with the central axis of the insertion section 2. In addition, the pivotal pin 56 coincides with the central axis of the insertion section 2. Even when the pivotal pins 54, 56 coincide with the central axis of the insertion section 2 in such a manner, positions of the jaws 60 and 61 are almost the same as those in the sixth embodiment and therefore there is no problem in use of a practical aspect.

With use of the above mentioned structure, the jaws 60, 61 are opened and closed in an almost similar way to that of the sixth embodiment. Since the pivotal hole 63d is not required to be eccentrically positioned, which makes mechanical processing in fabrication simplified and the cost reduced. Since the pivotal pin 54 located at the closest position to the fore end and the pivotal pin 56 located at the closest position to the base end are both on the central axis of the insertion section 2, no lateral force is produced by a component of force when a pulling force is imposed on the operating rode 8. As a result, loss of a force caused by friction is reduced. In addition, a trend to increase mechanical play due to enlargement of the hole 63f by abrasion over a long time in use is prevented from occurring.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope forceps comprising;
   an operating section for inputting an operating force;
   an insertion section fixedly connected to the operating section and adapted to be inserted into a channel of an endoscope;
   an operating rod inserted in the insertion section so as to be movable forward or backward along a longitudinal direction of the insertion section, the operating rod having one end connected to the operating section for movement forward or backward in response to the operating force input from the operating section; and
   a forceps section disposed at a fore end of the insertion section, wherein the forceps section comprises:
a first jaw pivotally mounted at another end of the operating rod through a first pivotal shaft engaging both the first jaw and the operating rod; and
a second jaw pivotally mounted at the fore end of the insertion section through a second pivotal shaft engaging both the second jaw and the insertion section;
wherein the first jaw and the second jaw are pivotally mounted to each other through a third pivotal shaft engaging both the first jaw and the second jaw.

2. An endoscope forceps according to claim 1, wherein the third pivotal shaft is disposed between the first and second pivotal shafts in the longitudinal direction of the insertion section.

3. An endoscope forceps according to claim 1, wherein
the first jaw includes first and second holes formed in a base end side thereof, the first hole being formed closer to a fore end of the first jaw than the second hole, and the second jaw includes first and second holes formed in a base end side thereof one above the other,
the first pivotal shaft is inserted through the first hole of the first jaw and a hole formed in a fore end section of the operating rod to pivotally connect the first jaw and the operating rod;
the second pivotal shaft is inserted through the second hole of the second jaw and a hole formed in the fore end section of the insertion section to pivotally connect the second jaw and the insertion section, and
the third pivotal shaft is inserted through the second hole of the first jaw and the first hole of the second jaw to pivotally connect the first and second jaws.

4. An endoscope forceps according to claim 3, wherein,
when the fore ends of the first and second jaws are in contact with each other to define a perfectly closed condition, a center of the first pivotal shaft defines an origin (0,0) of an X,Y coordinate system having an X axis passing through the origin and extending along an axial direction of the insertion section and a Y axis passing through the origin and extending along a direction perpendicular to the X axis, a center of the second pivotal shaft has the coordinates (2a, −b) or a set of values in the vicinity thereof, and a center of the third pivotal shaft has the coordinates (a, b), wherein b/a>1.

5. An endoscope forceps according to claim 2, wherein
the first jaw includes first and second holes formed in a base end side the first hole being formed closer to a fore end of the first jaw than the second hole, and the second jaw includes first and second holes formed in a base end side thereof one above the other,
the first pivotal shaft is inserted through the first hole of the first jaw and a hole formed in a fore end section of the operating rod to pivotally connect the first jaw and the operating rod;
the second pivotal shaft is inserted through the second hole of the second jaw and a hole formed in the fore end section of the insertion section to pivotally connect the second jaw and the insertion section, and
the third pivotal shaft is inserted through the second hole of the first jaw and the first hole of the second jaw to pivotally connect the first and second jaws.

6. An endoscope forceps according to claim 5, wherein,
when the fore ends of the first and second jaws are in contact with each other to define a perfectly closed condition, a center of the first pivotal shaft defines an origin (0,0) of an X,Y coordinate system having an X axis passing through the origin and extending along an axial direction of the insertion section and a Y axis passing through the origin and extending along a direction perpendicular to the X axis, a center of the second pivotal shaft has the coordinates (2a, −b) or a set of values in the vicinity thereof and a center of the third pivotal shaft has the coordinates (a, b), wherein b/a>1.

7. An endoscope forceps according to claim 1, wherein
the first jaw includes first and second holes formed in a base end side thereof, the first hole being formed closer to a fore end of the first jaw than the second hole, and the second jaw includes first and second holes formed in a base end side thereof, the first hole of the second jaw being formed closer to a fore end of the second jaw than the second hole of the second jaw,
the first pivotal shaft is inserted through the second hole of the first jaw and a hole formed in a fore end section of the operating rod to pivotally connect the first jaw and the operating rod;
the second pivotal shaft is inserted through the first hole of the second jaw and a hole formed in the fore end section of the insertion section to pivotally connect the second jaw and the insertion section, and
the third pivotal shaft is inserted through the first hole of the first jaw and the second hole of the second jaw to pivotally connect the first and second jaws.

8. An endoscope forceps according to claim 7, wherein, when the fore ends of the first and second jaws are in contact with each other to define a perfectly closed condition, a center of the first pivotal shaft defines an origin (0,0) of an X,Y coordinate system having an X axis passing through the origin and extending along an axial direction of the insertion section and a Y axis passing through the origin and extending along a direction perpendicular to the X axis a center of the second pivotal shaft has the coordinates (−2b, ±c) or a set of values in the vicinity thereof, and a center of the third pivotal shaft has the coordinates (−b,a), wherein b/a>1 and a>c≧0.

9. An endoscope forceps according to claim 2, wherein
the first jaw includes first and second holes formed in a base end side thereof, the first hole being formed closer to a fore end of the first jaw than the second hole, and the second jaw includes first and second holes formed in a base end side thereof, the first hole of the second jaw being formed closer to a fore end of the second jaw than the second hole of the second jaw,
the first pivotal shaft is inserted through the second hole of the first jaw and a hole formed in a fore end section of the operating rod to pivotally connect the first jaw and the operating rod;
the second pivotal shaft is inserted through the first hole of the second jaw and a hole formed in the fore end section of the insertion section to pivotally connect the second jaw and the insertion section, and
the third pivotal shaft is inserted through the flat hole of the first jaw and the second hole of the second jaw to pivotally connect the first and second jaws.

10. An endoscope forceps according to claim 9, wherein, when the fore ends of the first and second jaws are in contact with each other to define a perfectly closed condition, a center of the first pivotal shaft defines an origin (0,0) of an X,Y coordinate system having an X axis passing through the origin and extending along an axial direction of the insertion section and a Y axis passing through the origin and extending along a direction perpendicular to the X axis, a center of the second pivotal shaft has the coordinates (−2b, ±c) or a set of values in the vicinity thereof, and a center of the third pivotal shaft has the coordinates (−b,a), wherein b/a>1 and a>c≧0.

11. An endoscope forceps comprising:

an operating section including a stationary handle and a movable handle pivotally connected to the stationary handle;

an insertion section including a bracing member in the shape of a rod mounted to the stationary handle, an operating force transmitting member in the shape of a rod disposed in parallel to the bracing member and having one end detachably mounted to the movable handle, and a support member detachably mounted to both the bracing member and the operating force transmitting member and held therebetween, for supporting the parallel disposition of the bracing member and the operating force transmitting member;

a forceps section disposed at a fore end of the insertion section; and positioning means for controlling a moving direction of the operating force transmitting member so that the operating force transmitting member moves only along an axial direction of the insertion section in response to operation of the movable handle, the operating force transmitting member being detachably mounted to the stationary handle by the positioning means, whereby the forceps section at the fore end of the insertion section is moved by forward or backward movement of the operating force transmitting member in response to operation of the movable handle.

12. An endoscope forceps according to claim 11, wherein the forceps section comprises:

a first jaw pivotally mounted at a fore end of the operating force transmitting member through a first pivotal shaft engaging both the first jaw and the operating force transmitting member; and a second jaw pivotally mounted at a fore end of the bracing member through a second pivotal shaft engaging both the second jaw and the bracing member, wherein the first jaw and the second jaw are pivotally mounted to each other through a third pivotal shaft engaging both the first jaw and the second jaw.

* * * * *